(12) United States Patent
Marquardt et al.

(10) Patent No.: US 10,408,675 B2
(45) Date of Patent: Sep. 10, 2019

(54) ENCLOSED BENCHTOP RAMAN SPECTROMETRY DEVICE

(71) Applicant: MarqMetrix Inc., Seattle, WA (US)

(72) Inventors: Brian James Marquardt, Seattle, WA (US); John Scott Van Vuren, Seattle, WA (US)

(73) Assignee: MarqMetrix, Inc., Seattle, WA (US)

( * ) Notice: Subject to any disclaimer, the term of this patent is extended or adjusted under 35 U.S.C. 154(b) by 16 days.

(21) Appl. No.: 15/897,754

(22) Filed: Feb. 15, 2018

(65) Prior Publication Data

US 2018/0231415 A1 Aug. 16, 2018

Related U.S. Application Data

(63) Continuation-in-part of application No. 15/434,002, filed on Feb. 15, 2017, now Pat. No. 9,958,324.

(51) Int. Cl.

| G01J 3/00 | (2006.01) |
|---|---|
| G01J 3/02 | (2006.01) |
| G01N 21/95 | (2006.01) |
| G01N 21/65 | (2006.01) |
| G01N 15/02 | (2006.01) |
| A61B 5/00 | (2006.01) |

(Continued)

(52) U.S. Cl.
CPC .......... *G01J 3/0202* (2013.01); *A61B 5/0082* (2013.01); *G01J 3/027* (2013.01); *G01J 3/0208* (2013.01); *G01J 3/0235* (2013.01); *G01J 3/0262* (2013.01); *G01J 3/0264* (2013.01); *G01J 3/44* (2013.01); *G01N 15/0227* (2013.01); *G01N 21/65* (2013.01); *G01N 21/95* (2013.01); *G01N 33/6851* (2013.01); *G01J 3/0291* (2013.01)

(58) Field of Classification Search
CPC ...... G01J 3/32; G01J 3/42; G01J 3/44; G01N 21/31; G01N 21/75; G01N 21/95; G01N 21/65; G01N 33/68; G01N 33/92; G01N 35/00; G01N 35/02; G01N 35/10
See application file for complete search history.

(56) References Cited

U.S. PATENT DOCUMENTS

| 6,583,879 B1 | 6/2003 | Berg et al. |
|---|---|---|
| 2014/0003579 A1 | 1/2014 | Berruyer |

(Continued)

OTHER PUBLICATIONS

PCT Invitation to Pay Additional Fees mailed Apr. 19, 2018 for PCT Application No. PCT/US17/31330, 2 pages.

(Continued)

*Primary Examiner* — Abdullahi Nur
(74) *Attorney, Agent, or Firm* — Lee & Hayes, P.C.

(57) ABSTRACT

An enclosed benchtop analytical device, as well as systems, processes, and techniques related thereto are disclosed. A benchtop analytical device can include an enclosure enclosing a probe and a sample. A compliance component can determine satisfaction of one or more compliance rules, such as a compliance rule relating to an enclosure being in an operable configuration based on a lid of the enclosure being closed. If the compliance rule(s) is determined to be satisfied, the compliance component may enable the release of optical energy for interrogation of the sample via the probe. In some embodiments, the enclosure can enclose a sample plate that can be used to conveniently and accurately retain a sample in a suitable position within the enclosure.

22 Claims, 19 Drawing Sheets

(51) Int. Cl.
*G01N 33/68* (2006.01)
*G01J 3/44* (2006.01)

(56) References Cited

U.S. PATENT DOCUMENTS

2016/0069919 A1* 3/2016 Holmes .................. G01N 21/07
                                                            506/2
2016/0161705 A1   6/2016 Marquardt et al.

OTHER PUBLICATIONS

PCT Search Report and Written Opinion dated Jun. 15, 2018, for PCT Application No. PCT/US18/18416, 9 pages.

* cited by examiner

ENCLOSED BENCHTOP RAMAN SPECTROMETRY DEVICE

CROSS REFERENCE TO RELATED APPLICATION

This application is a continuation-in-part of commonly assigned, co-pending U.S. patent application Ser. No. 15/434,002, filed Feb. 15, 2017. Application Ser. No. 15/434,002 is fully incorporated herein by reference.

TECHNICAL FIELD

The disclosed subject matter relates to enclosed benchtop analytical equipment, e.g., benchtop chemical analysis equipment having an enclosure. In some embodiments, the disclosed subject matter relates to optical analysis equipment, e.g., a Raman spectrometry device.

BACKGROUND

Conventional Raman spectrometers were often large industrial sized instruments. Developments in the fields of imaging and laser technologies have allowed Raman spectrometers to dramatically shrink in size, allowing for benchtop and even hand-held portable analytical equipment that can provide highly detailed analytical information to a user in the field. Despite these advances, the Raman spectrometer-to-sample interface of a conventional benchtop system is exposed to the external environment. As such, in an effort to accommodate safe and effective use of the Raman instrument, these conventional instruments are often used in special rooms to reduce ambient light, or they are placed in fume hoods to remove noxious vapors and fumes emanating from the sample. Often, an operator of a conventional Raman instrument uses laser-safe eye protection to shield his/her eyes from harmful light that may emanate from the spectrometer-to-sample interface. In some conventional systems, primitive enclosures in the form of a rudimentary lid or box can be used to block light transmission, which may help protect an operator's eyes and/or block ambient light.

However, these primitive solutions typically introduce challenges, such as, challenges in positioning a sample for analysis in a convenient manner, difficulty in automating sequential sampling, a lack of environmental control, and the like. For instance, once an operator of a conventional system blocks the spectrometer-to-sample interface with a primitive enclosure, there is typically no way of confirming the location of the sample has not changed. Furthermore, there is generally no way of sampling noxious samples short of placing the entire Raman instrument into a fume hood, and there is generally no way of regulating the environment of the sample without subjecting the entire Raman instrument to similar conditions by regulating the environment of the room in which the Raman instrument is located. The disclosure made herein is presented with respect to these and other considerations.

SUMMARY

Raman spectrometry typically experiences a great deal of loss in optical power between the interrogating optical energy and the returned optical energy. As such, optical energy sources, e.g., lasers, etc., are often quite powerful to allow for use of affordable detectors. While specialty detectors could allow for use of lower energy interrogation lasers, the cost of the detectors and special operating conditions causes this option to be less viable in a commercial setting. It will be appreciated that powerful lasers can be a danger to human tissue, particularly the human eye.

To this end, the subject disclosure relates to an enclosed benchtop analytical device, and methods of using the enclosed benchtop analytical device. The benchtop analytical device may include a probe that is configured to perform optical spectroscopy of a sample. Accordingly, an operator can place a sample within an enclosure of the benchtop analytical device at a position where it can be interrogated by the probe. A sample presentation component within the enclosure may be used for this purpose. With the sample in position, the operator may shut the lid of the enclosure, thereby enclosing the sample and the probe within the enclosure. A compliance component of the benchtop analytical device may confirm that the lid of the enclosure is completely shut before allowing the optical spectroscopy to commence. For example, the compliance component may enable performance of the optical spectroscopy via the probe in response to determining that a rule(s) is satisfied, such as a rule that is satisfied when the enclosure being in an operable configuration (e.g., the lid is closed). Thus, the compliance component controls (e.g., enables or disables) the release of optical energy via the probe such that optical energy is exclusively released from the probe in instances when it is appropriate (e.g., safe) to do so. This can allow for the designation of procedures, tolerances, and safety measures to be automatically monitored before allowing the analysis to proceed using the benchtop analytical device. Accordingly, operator safety is improved because the enclosure effectively shields the operator's eyes (and any other user's eyes) from any emanating optical energy, and the probe is prevented from releasing optical energy while the enclosure is open, thereby protecting nearby users and/or observers in the vicinity of the benchtop analytical device. This makes it efficient and convenient to perform optical spectroscopy of a sample in any environment where the benchtop analytical device is located.

In some embodiments, the sample presentation component within the enclosure of the benchtop analytical device may include a sample plate to receive and support the sample within the enclosure. This sample plate may be removable, and when placed in the enclosure, the sample plate may rest within a retaining area that is defined in a body of the enclosure. The sample plate may include features and/or mechanisms to ensure accurate and convenient positioning of the sample so that efficiency of performing optical spectroscopy of a sample within the enclosure is improved, and to ensure that the position of the sample does not change after closing the lid of the enclosure. For example, the sample plate may have a sloped surface that slopes from a highest point at a periphery of the sample plate to a lowest point at a location adjacent to the probe when the sample plate is disposed in the plate retaining area. This allows for leveraging the force of gravity to retain the sample at a suitable position on the sample plate (e.g., in a line of sight of, and/or in contact with a tip of, the probe) after the lid of the enclosure is closed. Additionally, or alternatively, the sample plate may have a flat surface with a recessed area defined in the flat surface of the sample plate, wherein a portion of the recessed area is positioned at a location adjacent to the probe when the sample plate is disposed in the plate retaining area. This recessed area helps retain the sample at a suitable position on the sample plate (e.g., in a line of sight of, and/or in contact with a tip of, the probe) after the lid of the enclosure is closed. In yet other embodiments, the sample plate may be associated with an adjustment mechanism to adjust the position of the sample relative to the probe, which allows for convenient positioning of the sample, and for retaining the sample at a suitable position after the lid of the enclosure is closed.

A benchtop analytical device (e.g., a benchtop Raman spectrometer) with an enclosure according to one or more of the disclosed embodiments can serve to improve the operation and implementation of Raman spectrometers by allowing for safer operation, improved automation, a wider degree of allowed samples, self-diagnosis of consumable elements, etc. Some disclosed embodiments allow the operator to exchange different sample presentation components (e.g., sample plates) within the enclosure to allow for interrogation of samples that are packaged in different types of packaging (e.g., differently-shaped packaging). For example, packaged medicine (pharmaceuticals) can be placed on an appropriate sample plate, which can then be placed in a plate retaining area defined in a body of the enclosure to allow for optical interrogation of pharmaceutical samples. In this scenario, an operator may simply select a verify button to commence optical spectroscopy of the sample within the enclosure, and one or more results of the analysis may be presented to the operator (e.g., on a display screen). The results presented to the operator may indicate whether the type of sample (such as a type of medication) is verified via optical spectroscopy (e.g., by determining that an obtained Raman spectra matches a known Raman spectra of the type of sample), and/or whether the concentration of the sample is verified via optical spectroscopy. This is particularly useful in the pharmaceutical industry, for example, where the wrong types of medications and/or the wrong concentrations of medications can mysteriously find their way into standard pharmaceutical packaging that is distributed and eventually used to treat patients in various settings, such as hospitals.

To the accomplishment of the foregoing and related ends, the disclosed subject matter, then, includes one or more of the features hereinafter more fully described. The following description and the annexed drawings set forth in detail certain illustrative aspects of the subject matter. However, these aspects are indicative of but a few of the various ways in which the principles of the subject matter can be employed. Other aspects, advantages and novel features of the disclosed subject matter will become apparent from the following detailed description when considered in conjunction with the provided drawings.

BRIEF DESCRIPTION OF DRAWINGS

The subject disclosure is now described with reference to the drawings, wherein like reference numerals are used to refer to like elements throughout. In the following description, for purposes of explanation, numerous specific details are set forth in order to provide a thorough understanding of the subject disclosure. It may be evident, however, that the subject disclosure may be practiced without these specific details. In other instances, well-known structures and devices are shown in block diagram form in order to facilitate describing the subject disclosure.

DETAILED DESCRIPTION

It will be noted that the disclosed embodiments can be presented separately for clarity and brevity but that combinations of the disclosed embodiments are also considered to be within the scope of the present disclosure, for example, a first embodiment can disclose an enclosure with a viewport and a second embodiment can disclose an enclosure with an environmental control unit, and a third embodiment can disclose an enclosure with an imaging system, accordingly, an embodiment with both a viewport and an environmental control is considered, an embodiment with both a viewport and an imaging system is considered, an embodiment with an imaging system and an environmental control is considered, and an embodiment with a viewport, an environmental control, and an imaging system is considered, etc. improve the efficiency of Raman spectral analysis, lower training costs, improve safety, allow for analysis of a wider range of samples, etc.

Figure 1:
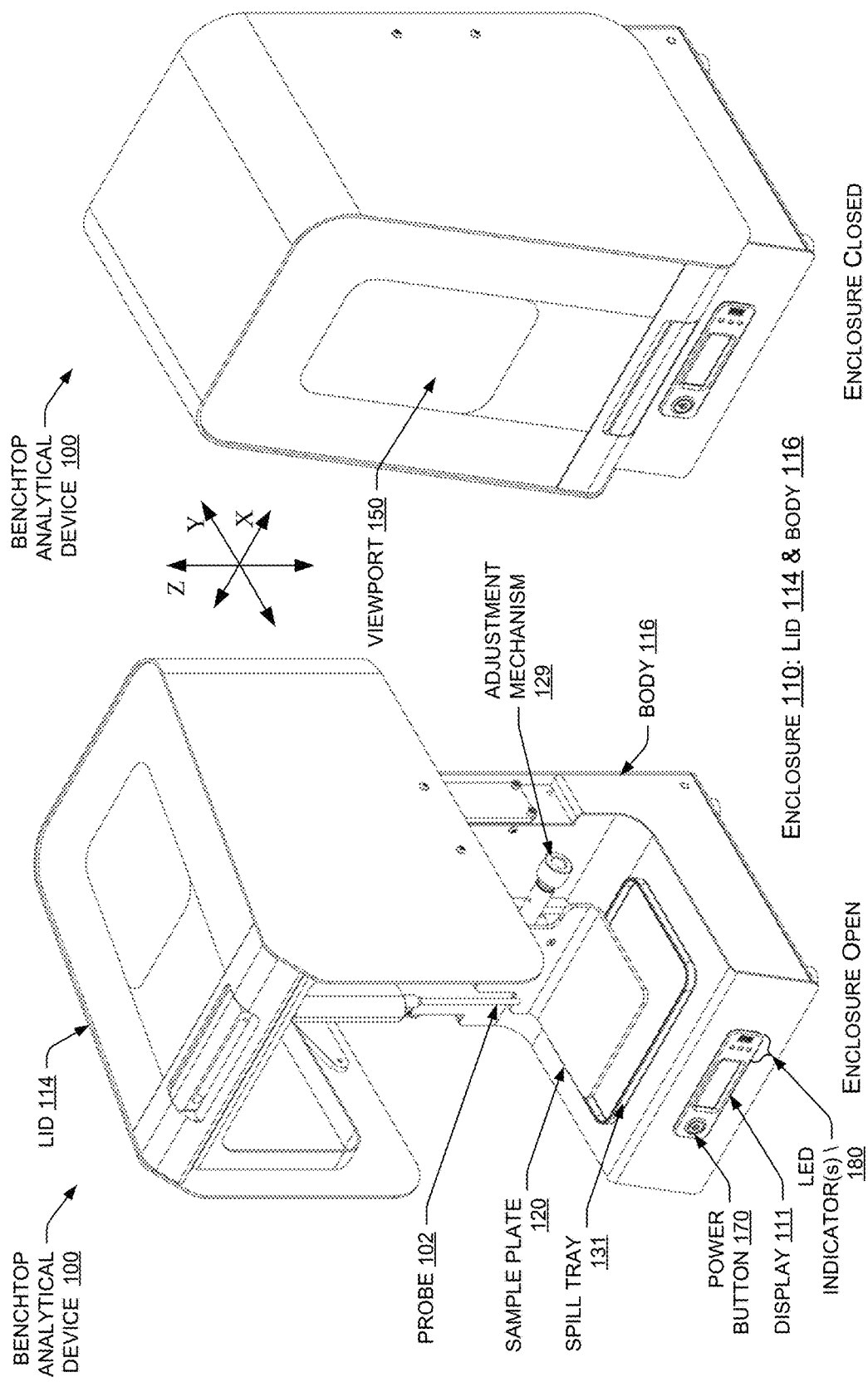
FIG. 1 illustrates a perspective view of an example benchtop analytical device including an enclosure shown in both an open and a closed state, the enclosure (in the closed state) to enclose a sample and a probe, in accordance with aspects of the subject disclosure.

FIG. 1 illustrates a perspective view of an example benchtop analytical device 100 including an enclosure 110 that can be in either an opened or a closed state. The enclosure 110 of the benchtop analytical device 100 may (in the closed state) enclose a probe 102, in accordance with aspects of the subject disclosure. The benchtop analytical device 100 disclosed herein may facilitate non-contact-type optical interrogation of a sample from a distance, e.g., a focal point of the incident beam may be a determined distance from a most distal portion (e.g., the tip) of the probe 102. With non-contact-type optical interrogation, the sample itself (or a package containing the sample) may nevertheless contact the tip of the probe 102, but the sample (or its package) does not have to contact the tip of the probe 102 in non-contact-type optical interrogation. Various examples described herein disclose the "sample" being "in contact with" the probe 102. It is to be appreciated that the "sample" being "in contact with" the probe 102 can mean that the sample itself is in contact with the probe 102, or, in the alternative, that a package (or container) containing the sample is in contact with the probe 102. In the latter case, the package containing the sample may be transparent to allow for optical interrogation of the sample within the package. Non-contact-type optical interrogation may be used to analyze samples while they remain packaged within their transparent packages because the focal point of the incident beam may be located inside the package (i.e., a determined distance from the tip of the probe 102) when the sample package is positioned near (i.e., within a threshold distance of), or placed in contact with, the tip of the probe 102.

In some embodiments, the probe 102 may facilitate contact-type optical interrogation of a sample. Contact-type optical interrogation is when a most distal portion (e.g., the tip) of the probe 102 is in contact with the sample during optical interrogation. An example probe 102 that facilitates contact-type optical interrogation of a sample is a probe 102 having a spherical lens for directing optical energy at a sample interface that coincides with a point where the sample makes contact with the most distal portion (e.g., the tip) of the probe 102.

As shown in FIG. 1, the enclosure 110 may include a lid 114 and a body 116. The lid 114 may be movable between an opened position and a closed position relative to the body 116 of the enclosure 110. The lid 114 is shown in the open position on the left side of FIG. 1, and in the closed position on the right side of FIG. 1. A contact sensor disposed in or on the enclosure 110 may determine when the lid 114 of the enclosure 110 is in the closed position (and also when the lid 114 is not in the closed position), and the contact sensor may provide an indication to a compliance component of the benchtop analytical device 100 to indicate when the enclosure 110 is in compliance with a compliance rule relating to the enclosure being in an operable configuration (e.g., the enclosure 110 may be in an operable configuration when the lid 114 of the enclosure 110 is in the closed position). Before optical energy is released or emitted via the probe 102 to perform optical spectroscopy of a sample in the enclosure 110, the compliance component may determine whether the compliance rule(s) is satisfied, and if so, enable the release of the optical energy via the probe 102. The compliance rule relating to an operable configuration of the enclosure 110 may be one of a group of compliance rules that are to be concurrently satisfied before proceeding with the optical spectroscopy of the sample, as described herein.

In an aspect, the lid 114 may include a viewport 150. In an aspect, the viewport 150 can be optically transparent at select wavelengths to allow direct viewing of an analysis with operator safety and reduction of artifacts in the captured spectrum. As an example, the viewport 150 can include a laser safe window to attenuate laser light that can escape the sample interface, which can protect an operator. As another example, the viewport 150 can include a shutter, sliding plate, etc., that can physically block light transmission. In this example, the operator can directly view the sample, for example to position it, then can provide an input, e.g., press a start (or verify) button, etc., that can trigger a shutter to close, the analysis to proceed, and then the shutter to open. The shuttering process can be kept brief, being perhaps just slightly longer than the time needed to interrogate the sample optically. In an aspect, the shutter can 'blink' to protect the operator from laser light and to shield the interface from ambient light. Whereas a compliance component can enable the release of the laser energy via the probe 102 when the shutter is closed, the action of triggering the shutter can in effect also cause the laser to fire on the sample. It will be noted that heuristic timing can be incorporated into the example to provide for a slight delay after the triggering of the shutter before lasing the sample begins, and correspondingly, a slight delay between the end of lasing and the reopening of the shutter. The operator can directly view the sample/probe interface via the viewport 150 while the lid 114 of the enclosure 110 is closed. Other embodiments described herein use additional imaging components to extend the human senses in a similar manner, allowing analysis of fragile or dangerous samples, such as in an automated manner with a variety of instrumental modes, while monitoring a condition of the instrument and providing a safer and more comfortable bench top analysis environment.

The body 116 of the enclosure 110 may include various components and electronics of the system, such as components of a Raman spectrometer to process/analyze the results of Raman analysis of a sample within the enclosure 110. The enclosure 110 may be part of the benchtop analytical device 100 configured to allow an operator to perform analyses of samples. For instance, the benchtop analytical device 100 may further include, and the enclosure 110 may be communicatively coupled (wired or wirelessly) to, a computer having a display for presentation of user interface controls and analysis results (e.g., Raman spectra, sample determinations, etc.). In some embodiments, such a computer can be integrated or embedded in the body 116 of the enclosure 110, and the enclosure 110 may include an embedded display, such as the display 111 shown in FIG. 1.

The enclosure 110 may include various input and/or output components, such as a power button 170 that an operator can actuate (e.g., press) to power on the electronics of the enclosure 110 (and electronics of the benchtop analytical device 100 in general). The enclosure 110 may further include one or more light emitting diode (LED) indicators 180 to indicate various things, such as to indicate that power is on, to indicate that sample analysis (e.g., optical spectroscopy) is in progress, to indicate that the enclosure 110 is in an operable configuration (e.g., that the lid 114 is in the closed position), etc.

The probe 102 may be mounted on the body 116 and oriented in a downward facing direction. That is, the probe 102 may point in the negative z-direction, as shown in FIG. 1, by including optical elements (e.g., a lens(es), etc.) that direct optical energy—in the form of laser light—from an excitation source in the negative z-direction (or downward direction), and that collect scattered light reflected from a sample in the positive z-direction.

In some embodiments, the probe 102 can include an optical element to direct optical energy at a sample. As an example, the probe 102 can be a BallProbe® (MarqMetrix Inc., Seattle, Wash.) for Raman immersion testing, contact Raman testing, etc. The probe 102 can include other technologies, e.g., an infrared (IR) probe, a resistance probe, a conductivity probe, a pH probe, a biomarker probe, etc., without departing from the scope of the presently disclosed subject matter as will be appreciated by one of skill in the relevant arts.

Moreover, while this disclosure is generally presented in terms of Raman spectroscopy for clarity and brevity, it is asserted that similar advantages can be provided for other benchtop instruments, including those using other optical analysis techniques such as ultraviolet/visible (UV-Vis), near infrared (NIR), mid-infrared (FTIR), fluorescence, etc., and that all such other uses are within the scope of the present disclosure despite not being explicitly recited. Furthermore, in some embodiments, the disclosed subject matter can perform Raman spectroscopy serially or in parallel with other optical analysis techniques such as UV-Vis, NIR, FTIR, fluorescence, etc., e.g., a Raman spectrum can be captured along with another optical analysis for the same sample at substantially the same time, such that an operator does not need to move the sample from a Raman instrument to a NIR instrument, to a FTIR instrument, etc. In some embodiments, the disclosed subject matter can support Raman performed in series or in parallel for multiple excitation energies, e.g., 532 nm, 785 nm, 1064 nm, etc. Further still, some embodiments can combine imaging with Raman spectra, e.g., a picture of the sample and a Raman spectrum mapped to the picture.

The enclosure 110 may further include a sample plate 120 (an embodiment of a sample presentation component, as disclosed herein). The probe 102 and/or sample plate 120 may move relative to the other, e.g., in the x-, y-, and z-planes, rotationally, etc. This can allow a sample to be positioned relative to the probe 102 to enable optical analysis, e.g., Raman spectroscopy, IR spectroscopy, UV-Vis spectroscopy, etc., at determined locations of the sample.

In an aspect, sample plate 120 can move relative to the probe 102, e.g., in the x-axis, y-axis, z-axis, rotationally, etc., so as to be able to present different portions of a sample, different samples, etc., for analysis via probe 102. In an example, a position of sample plate 120 and probe 102 can be determined. The positon can be employed to determine that the sample is appropriately oriented for optical interrogation. In some example embodiments, sample plate 120 can include a multi-well plate. This can enable analysis of samples in one or more wells of the multi-well plate.

In some embodiments, the disclosed subject matter contemplates that the position of the optical interrogation of a sample can be altered. In an aspect, this can be achieved by moving the probe 102 relative to the sample, moving the sample relative to the probe 102, or both moving the sample and the probe 102 relative to each other. In this disclosure, except where explicitly disclosed as being exclusive of other relative movement, descriptions of moving the sample can be accomplished by these or other techniques, e.g., changing the focal position of the interrogating optical energy with or without movement of the probe 102 or the sample, etc. In effect, the present disclosure is, in part, directed to analysis of different portions of a sample within the enclosed area of the disclosed device or system. As an example, where a sample is liquid and the probe 102 is dipped in to the liquid, e.g., in-situ analysis, different portions of the sample can be analyzed at least by moving the probe 102 tip in the sample, moving the sample around the probe 102, moving both the probe 102 and the sample, changing a focal length of the interrogating laser to sample a different area of the sample with/without moving the sample and/or probe 102, flowing the sample past the probe 1002, etc.

In some embodiments, movement of sample plate 120 (in at least one direction) can be enabled by an adjustment mechanism 129 (such as a dial coupled to a translation mechanism). The adjustment mechanism 129 can be used (e.g., manipulated, rotated, etc.) by an operator while the lid 114 is in the opened position to cause movement (e.g., translational movement, such as along the z-axis) of the sample plate 120. This allows for convenient and accurate positioning of the sample relative to the probe 102, and it ensures that the position of the sample does not change after closure of the lid 114. A compliance component of the benchtop analytical device 100 can determine whether the enclosure 110 is closed and/or whether the probe 102 is in contact with a sample placed on the sample plate 102 using the various techniques described herein. In an aspect, probe 102 can move relative to sample plate 120, e.g., in the x-axis, y-axis, z-axis, rotationally, etc., so as to be able to access different portions of a sample, different samples, etc., for analysis. The enclosure 110 may further include a spill tray 131 disposed underneath the sample plate 120 to catch or collect any of the sample that spills over the edges of the sample plate 120. This spill tray 131 may be removable so as to discard any contents (e.g., spilled sample) collected therein.

Figure 2:
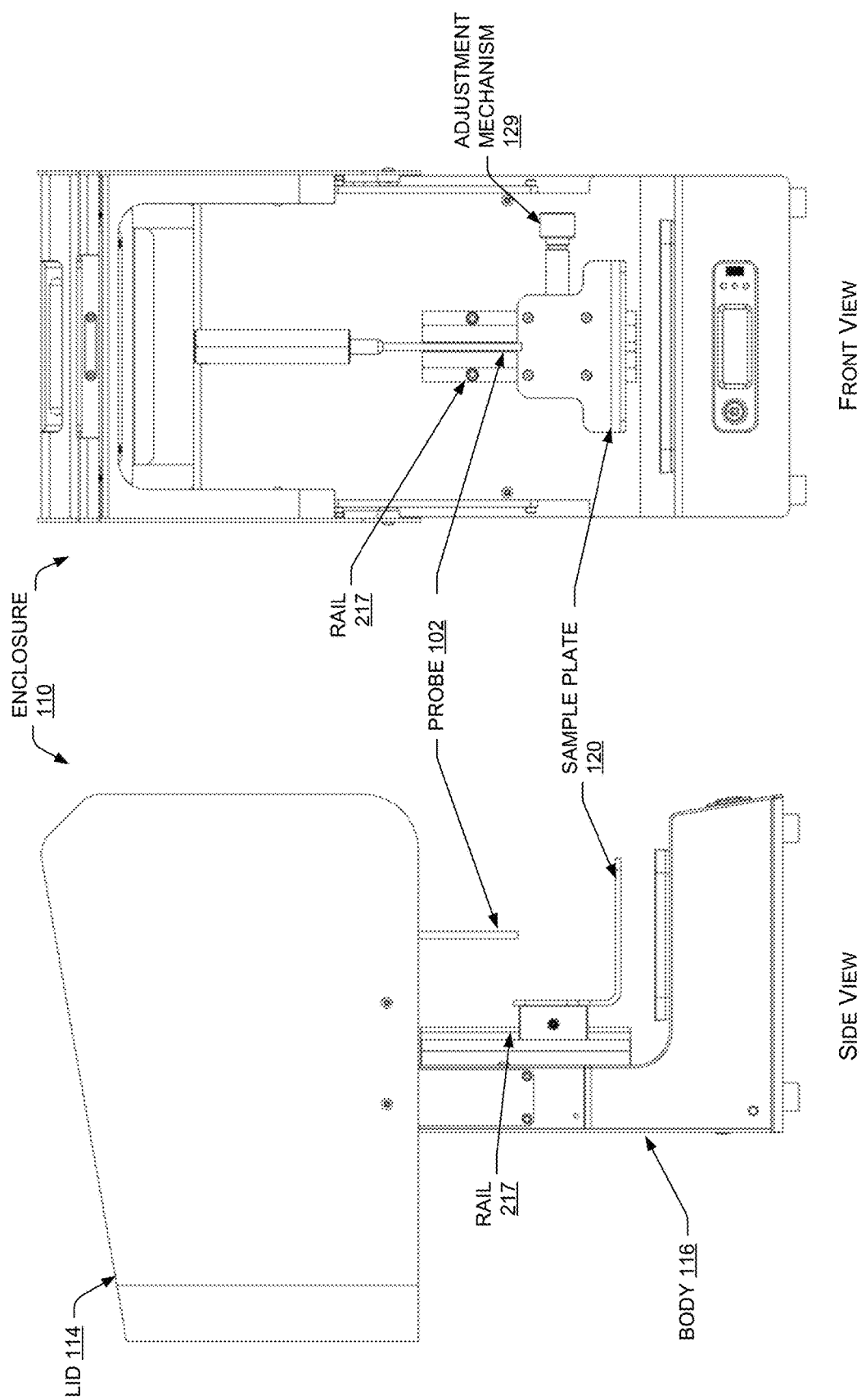
FIG. 2 illustrates side and front views of the example enclosure of the benchtop analytical device of FIG. 1, in accordance with aspects of the subject disclosure.

FIG. 2 illustrates side and front views of the example enclosure 110 of the benchtop analytical device 100 introduced in FIG. 1, in accordance with aspects of the subject disclosure. The side view (shown on the left side of FIG. 2) depicts the enclosure 110 in an opened state where the lid 114 is fully opened to reveal the interior of the enclosure 110. The front view (shown on the right side of FIG. 2) also depicts the enclosure 110 in the opened state where the lid 114 is fully opened to reveal the interior of the enclosure 110.

As shown in FIG. 2, a rail 217 on the body 116 of the enclosure 110 may allow the sample plate 120 to be mounted thereon, and may allow the sample plate 120 to move translationally in the positive or negative z-direction (i.e., up or down). The adjustment mechanism 129 may be used by an operator while the enclosure 110 is opened for making such large-scale position adjustments so as to position the sample plate 120 so that the probe 102 is at least close to (e.g., within a few millimeters of), or in contact with, the sample supported by the sample plate 120. After closing the enclosure 110, the operator may be able to make fine-tuned, or small-scale, adjustments, if necessary, to either or both of the sample plate 120 and/or the probe 102. The operator may utilize a remote or external control mechanism that controls the movement of the sample plate 120 and/or the probe 102 in small increments. In an example, the operator can see through the viewport 150 while he/she uses external adjustment controls, an imaging component, and/or an illumination component, etc., to adjust the position relative position of the sample plate 120 and the probe 102. FIG. 2 shows an example enclosure 110 having a probe 102 configured to perform contact-type optical interrogation of a sample by a most distal portion of the probe 102 being in contact with the sample at the sample interface during optical interrogation. The benchtop analytical device 100, including the enclosure 110, can be moved by an operator to any suitable location and utilized to perform optical spectroscopy of samples, providing convenient portability to an operator of the benchtop analytical device 100.

Figure 3:
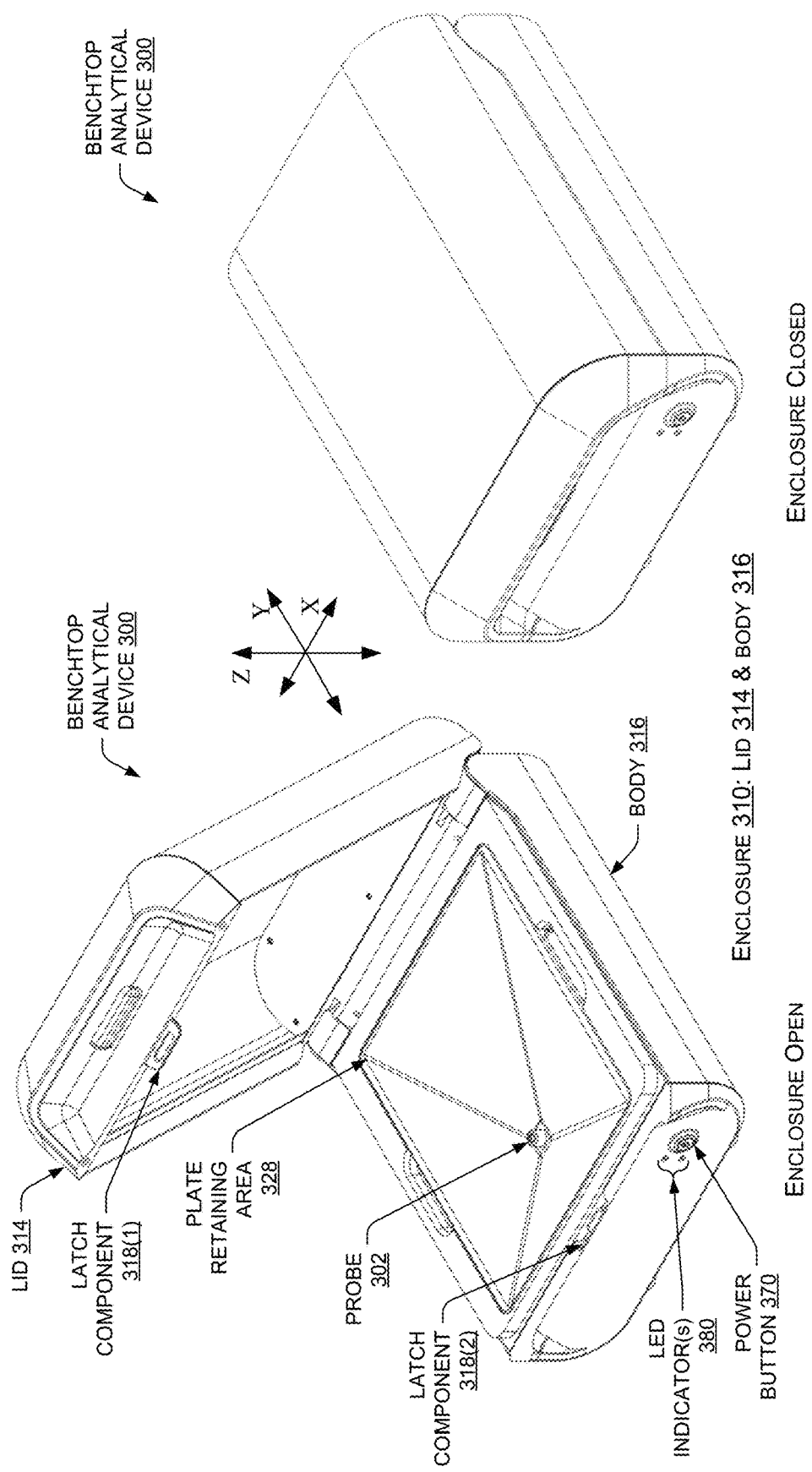
FIG. 3 illustrates a perspective view of an example benchtop analytical device including an enclosure in both an open and a closed state, the enclosure (in the closed state) to enclose a sample and a probe, in accordance with aspects of the subject disclosure.

FIG. 3 illustrates a perspective view of an example benchtop analytical device 300 according to another embodiment. The benchtop analytical device 300 may include an enclosure 310 that can be in either an open or a closed state. The enclosure 310 may enclose a sample and a probe 302, in accordance with aspects of the subject disclosure. The enclosure 310 may represent at least part of the benchtop analytical device 300 (e.g., an analytical instrument for performing Raman spectroscopy). The enclosure 310 may include a lid 314 and a body 316. The lid 314 may be movable, relative to the body 316, between an opened position and a closed position. The lid 314 is shown in the open position on the left side of FIG. 3, and in the closed position on the right side of FIG. 3. A two-part latch mechanism may include a first latch component 318(1) on the lid 314, and a second latch component 318(2) on the body 316, and these latch components 318 matingly engage when the lid 314 is moved into the closed position. A contact sensor disposed in the two-part latch mechanism 318, or elsewhere on the enclosure 310, may determine when the enclosure 310 is closed, and the contact sensor may provide an indication to a compliance component of the benchtop analytical device 300 to indicate when the enclosure 310 is in compliance with a compliance rule that the enclosure 310 is to be in an operable configuration before optical energy is released via the probe 302 to perform optical spectroscopy on a sample. The compliance rule that the enclosure 310 is in an operable configuration before proceeding with an analysis of a sample may be one of a group of compliance rules that are to be concurrently satisfied before proceeding with performance of the optical spectroscopy, as described herein.

The body 316 of the enclosure 310 may include various components and electronics of the system, such as components of a Raman spectrometer to process/analyze the results of Raman analysis of a sample within the enclosure 310. The enclosure 310 may be part of the benchtop analytical device 300 configured to allow an operator to perform analyses of samples. For instance, the enclosure 310 may be communicatively coupled (wired or wirelessly) to a computer having a display for presentation of user interface controls and analysis results (e.g., Raman spectra, sample determinations, etc.). In some embodiments, such a computer can be integrated or embedded in the body 316 of the enclosure 310, and the enclosure 310 may include an embedded display.

The enclosure 310 may include various input and/or output components, such as a power button 370 that an operator can actuate (e.g., press) to power on the electronics of the enclosure 310 (and/or electronics of the benchtop analytical device 300 in general). The enclosure 310 may also include one or more LED indicators 380 to indicate various things, such as to indicate that power is on, to indicate that sample analysis is in progress, to indicate that the enclosure 310 is in an operable configuration, etc.

The probe 302 may be mounted on the body 316 and oriented in an upward facing direction. That is, the probe 302 may point in the positive z-direction, as shown in FIG. 3, by including optical elements (e.g., a lens(es), etc.) that direct laser light from an excitation source in the positive z-direction (or upward direction), and that collect scattered light reflected from a sample in the negative z-direction. The probe may include a non-spherical lens (e.g., a lens having a flat surface at a distalmost point of the lens) for enabling non-contact-type optical interrogation of a sample (e.g., by creating a focal point of an incident beam that is a determined distance from a tip of the probe 302).

A plate retaining area 328 may be defined in the body 316 of the enclosure 310 and may surround the probe 302. The plate retaining area 328 may have a sloped surface that slopes downward (i.e., in the negative z-direction) from a highest point at a periphery of the body 316 to a lowest point adjacent to the probe 302. This sloped contour of the plate retaining area 328 can allow for sample plates of various designs/shapes, etc. to be placed in the plate retaining area, and can also allow for providing a degree of separation (if separation is desired) between the tip of the probe 302 and a sample when a sample plate is placed in the plate retaining area 328.

Figure 4:
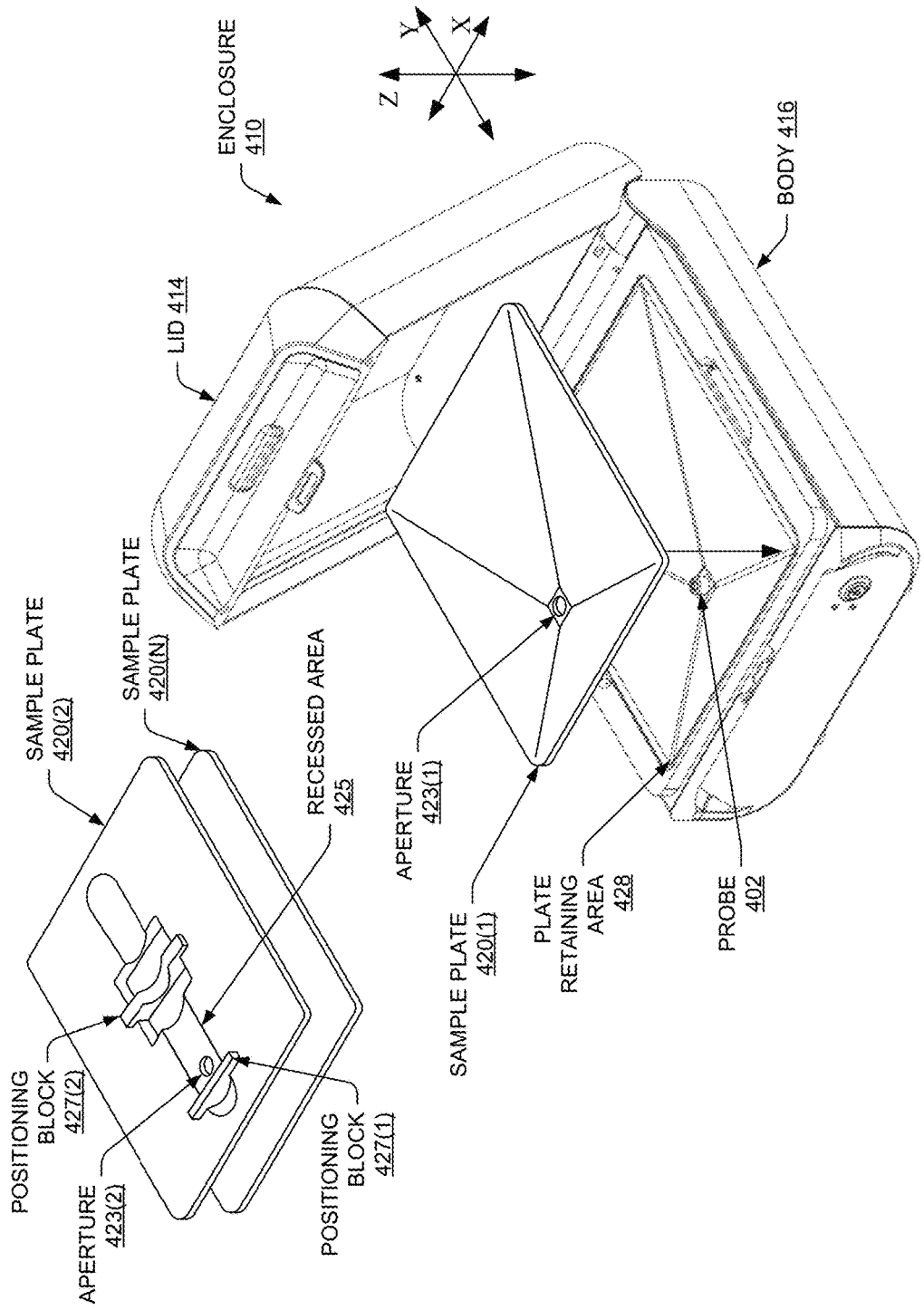
FIG. 4 illustrates a perspective view of an example enclosure of a benchtop analytical device, and example sample plates that can be removably disposed within the enclosure, in accordance with aspects of the subject disclosure.

FIG. 4 illustrates a perspective view of an example enclosure 410, and an example sample plate 420(1) being placed in the enclosure 410, in accordance with aspects of the subject disclosure. The enclosure 410 may have a plate retaining area 428, which may be the same as, or similar to, the plate retaining area 328 described with reference to FIG. 3. The plate retaining area 428 may be configured (e.g., shaped) to receive various sample plates 420 (one at a time), such as the first sample plate 420(1), the second sample plate 420(2), and possibly additional sample plates 420, such as any number of "N" sample plates 420(1)-(N) that may be exchanged for one another and placed within the enclosure 410. Thus, a sample plate 420 may be disposed on the body 416 of the enclosure 410 and within the plate retaining area 428 in order to support a sample thereon for interrogation of the sample via the probe 402. The individual sample plate 420 may be rectangular in shape and configured to support a sample (e.g., a liquid sample in a package). The individual sample plate 420 may be shaped similarly to the shape of the plate retaining area 428 to fit securely on the body and within the plate retaining area 428. Although FIG. 4 shows an example of multiple rectangular-shaped sample plates 420 that are to be placed in a rectangular-shaped plate retaining area 428 of the enclosure 410, it is to be appreciated that any suitable shape besides rectangular can be utilized for the sample plate(s) 420 and the plate retaining area 428.

Furthermore, an aperture 423(1) may be defined in the sample plate 420(1). The aperture 423(1) may be defined in a location on the sample plate 420(1) that is aligned (in the vertical, z-direction) with the probe 402 when the sample plate 420(1) is placed in the enclosure 410. An aperture 423(2) may be defined in the sample plate 420(2) in a similar manner. When a sample plate, such as the sample plate 420(1), is placed in the enclosure 410, the probe 402 is inserted (or disposed) within the aperture 423(1) of the sample plate 420(1). Furthermore, when the sample plate 420(1) is placed in the enclosure 410, a sample can be positioned over the aperture 423(1) of the sample plate 420(1), and on the topside of the sample plate 420(1). In this manner, the probe 402 (being vertically oriented and pointing in an upward (i.e., positive z) direction) may interrogate the sample from underneath the sample when the sample plate 420(1) is disposed on the body 416 of the enclosure 410 within the plate retaining area 428. In the example configuration shown in FIG. 4, an operator can conveniently place a sample (e.g., a pharmaceutical contained in a package) on the sample plate 420(1) such that the sample is positioned over the aperture 423(1), and the sample is held in place against the sample plate 420(1) by the force of gravity. The operator may then close the lid 414 of the enclosure 410 and the analysis may proceed (e.g., after a compliance component determines that the lid 414 is in the closed position) by directing laser light via the probe 402 at the sample while the enclosure 410 is closed, and by collecting scattered light via the probe 402.

Figure 5:
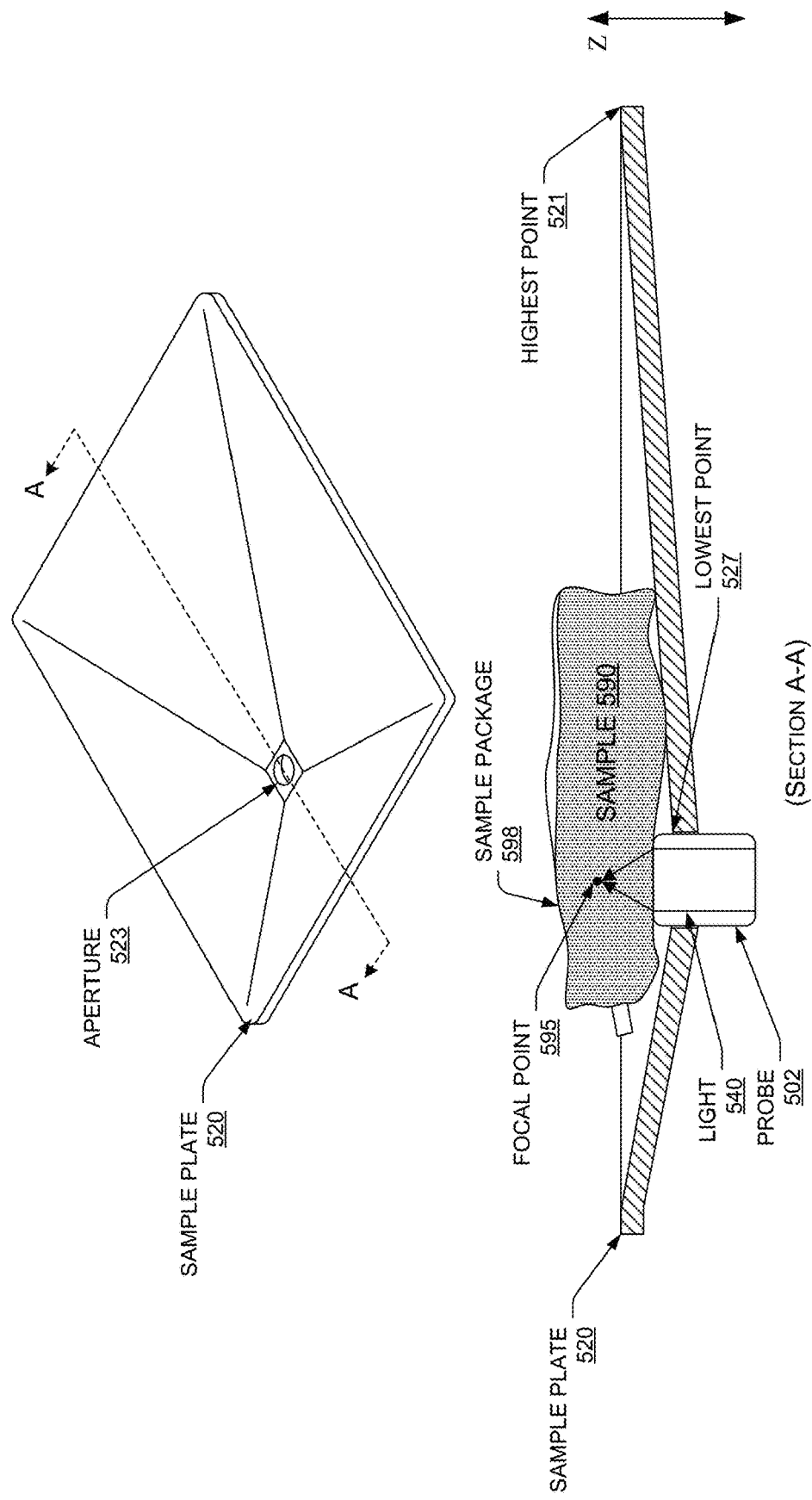
FIG. 5 illustrates a perspective view and a cross-sectional view, taken along section line A-A, of an example sample plate that is implemented in a benchtop analytical device where a probe is disposed within an aperture of the sample plate, and a sample is placed on a topside of the sample plate.

Turning briefly to FIG. 5, a cross-sectional view, taken along section line A-A, of an example sample plate 520 is shown with a probe 502 disposed through the aperture 523 of the sample plate 520, such as when the sample plate 520 is implemented in a benchtop analytical device, and when a sample 590 is placed on the sample plate 520. As shown in FIG. 5, the probe 502 may direct laser light in the positive z-direction at a focal point 595 that is a determined distance from a most distal end of the probe 502. The example of FIG. 5 shows a liquid sample 590 contained in a transparent sample package 598. This may represent a packaged pharmaceutical that includes a liquid sample 590 within a transparent plastic package 598. This is also an example where the sample 590 is considered to be in contact with the probe 502 by virtue of the sample package 598 being in contact with the probe 502. Thus, the "sample 590 being in contact with the probe 502," as used herein, can be interpreted as the configuration shown in FIG. 5. The focal point 595 of the excitation beam of laser light 540 may be at a point within the sample package 598 so that the sample 590 within the package is interrogated (rather than interrogating the sample package 598 itself). The sloped contour of the surface of the sample plate 520 helps to ensure that the focal point 595 will be at a point within the sample 590 instead of a point within an air pocket within the sample package 598, for example. That is, the upward slope causes any air pockets/bubbles to move to the side or the edge of the sample package 598, thereby maximizing the depth/height of sample 590 (e.g., liquid sample 590) over the location of the aperture 523 (and hence over the probe 502). The transparent nature of the sample package 598 allows the laser light 540 to pass through the sample package 598 and to excite the molecules of the sample 590 within the sample package 598 at the focal point 595, rather than focusing the excitation beam on the package material itself. Although sample plates 520 having an aperture 523 are depicted in the Figures, it is to be appreciated that a sample plate without an aperture can be utilized, such as by being transparent to allow for optical interrogation through the sample plate. In this case, the probe 502 would be disposed on an underside of the sample plate, rather than through the sample plate where the tip of the probe 502 can extend above a top surface of the sample plate 520, as depicted in FIG. 5.

FIG. 5 also illustrates how the sample plate 520 can have a sloped (top) surface that slopes from a highest point 521 at a periphery of the sample plate 520 to a lowest point 527 at a location adjacent to the aperture 523 (and hence at a location adjacent to the probe 502 when the sample plate 520 is disposed on the body 416 of the enclosure 410 within the plate retaining area 428). Furthermore, as mentioned above, a tip of the probe 502 may extend above the lowest point 527 of the sloped surface of the sample plate 520 when the sample plate 520 is disposed on the body 416 of the enclosure 410 within the plate retaining area 428. As such, the sample 590 (or, more specifically, the package 598 containing the sample 590) may contact the tip of the probe 520 when the sample 590 is placed on the topside of the sample plate 520 over the aperture 523. In other configurations, the tip of the probe 502 may not extend above the lowest point 527 of the sloped surface of the sample plate 520. For example, the tip of the probe 502 may terminate at a level that is flush with the lowest point 527 of the sloped surface of the sample plate 520, or below the lowest point 527 of the sloped surface of the sample plate 520. In these configurations, the tip of the probe 502 may not contact a sample 590 (or, more specifically, the package 598 containing the sample 590) when the sample 590 is placed on the sample plate 520, and when the sample plate 520 is placed in the plate retaining area 428 of the enclosure 410.

With reference again to FIG. 4, in an example, multiple exchangeable sample plates 420(1)-(N) are depicted. As shown, the second sample plate 420(2) includes a flat surface with a recessed area 425 defined in the flat surface. The recessed area 425 defined on the flat surface of the sample plate 420(2) may be shaped in such a way so as to receive a particular type of sample (e.g., a sample contained in a package having a particular shape). For instance, samples may be packaged in differently-shaped containers. In an illustrative example, a liquid pharmaceutical can be packaged in an intravenous (IV) bag, a syringe, or any other suitable type of container, package, or device. Accordingly, the first sample plate 420(1) may be configured to accommodate an IV bag, while the second sample plate 420(2) may include a recessed area 425 shaped to accommodate a syringe. Although examples of samples plates 420 are shown as having either a sloped surface (e.g., sample plate 420(1)) or a recessed area 425 defined in a flat surface of the sample plate 420 (e.g., sample plate 420(2)), the sample plate 420, in at least some aspects, may have a flat surface without a recessed area, or a surface that is not sloped (i.e., a substantially flat surface). In these aspects, the sample plate 420 with a substantially flat surface may still include an aperture 423 through which the probe 402 can analyze a sample.

The second sample plate 420(2) is also shown as including multiple positioning blocks 427(1) and 427(2) that the operator can manipulate to adjust the position of a syringe that includes a sample therein so that the sample in the syringe can be positioned over the aperture 423(2). The positioning blocks 427(1) and 427(2) may be slidingly coupled to, or engaged with, the sample plate 420(2), such as by using a magnetic coupling mechanism, a dovetailed slot, or the like. In this manner, the first sample plate 420(1) can be placed in the enclosure 410 to perform a first analysis by interrogating a liquid sample packaged in an IV bag. Subsequently, the operator can remove the first sample plate 420(1) from the enclosure 410 and replace it with the second sample plate 420(2) to interrogate a liquid sample packaged in a syringe. Moreover, a compliance component of the benchtop analytical device can, in some embodiments, check for the presence of a sample plate 420 to determine if the (correct) sample plate 420 is placed within the enclosure 410 before allowing the analysis to proceed. The compliance component may additionally, or alternatively, check for the presence of a sample to determine if the (correct) sample is placed within the enclosure 410 before allowing the analysis to proceed. In an illustrative example, the operator may indicate, via user input to a user interface, that he/she would like to analyze a sample packaged in an IV bag. The first sample plate 420(1) that is configured to accommodate samples packaged in IV bags, may be associated with a machine-readable code (e.g., a code printed on the sample plate 420(1)). Upon placing the correct sample plate 420(1) within the enclosure 410, a code reader of the enclosure 410 may read the machine-readable code (e.g., a bar code, a quick response (QR) code, etc.) and determine whether the code matches a code corresponding to IV bag packaging. This information may be used by the compliance component to determine whether the sample plate 420(1) is in compliance with a compliance rule by being the correct sample presentation component 420. In other embodiments, a sensor (e.g., an optical detector, etc.) may be configured to detect the presence of a sample plate 420 within the enclosure 410 for purposes of satisfying a compliance rule that a sample plate 420 (e.g., any sample plate) is to be placed in the enclosure 410 before the analysis proceeds. A weight or pressure sensor may be used to determine if and when a sample plate 420(1) and/or a sample has been placed in the enclosure 410 for purposes of satisfying one or more of the compliance rules described herein. In some embodiments, the sample plates 420 are disposable or single-use sample plates 420, such as by being made of a relatively cheap plastic or compostable material that is easy and cost effective to manufacture (e.g., via injection molding) at scale. Disposable sample plates 420 may be used in environments where sterility and cleanliness is of the utmost importance, such as in situations where chemotherapy medicine is being analyzed.

The benchtop analytical device 300 may be optimized to analyze (by performing optical spectroscopy) a sample through packaging. Thus, samples that are typically packaged in containers/packaging can be placed in the enclosure 310/410 without removing the sample 590 from its sample package 598. This is convenient for an operator using the benchtop analytical device 300/400 in certain settings, such as to analyze medications or pharmaceuticals in transparent packaging, to analyze food or drink that is packaged in transparent packaging, etc. The enclosure 310/410 is also easy for an operator to move from one location to another, making it convenient to perform optical spectroscopy on samples at any suitable location (e.g., in a hospital, a pharmacy, a restaurant, a manufacturing plant, etc.).

Figure 6:
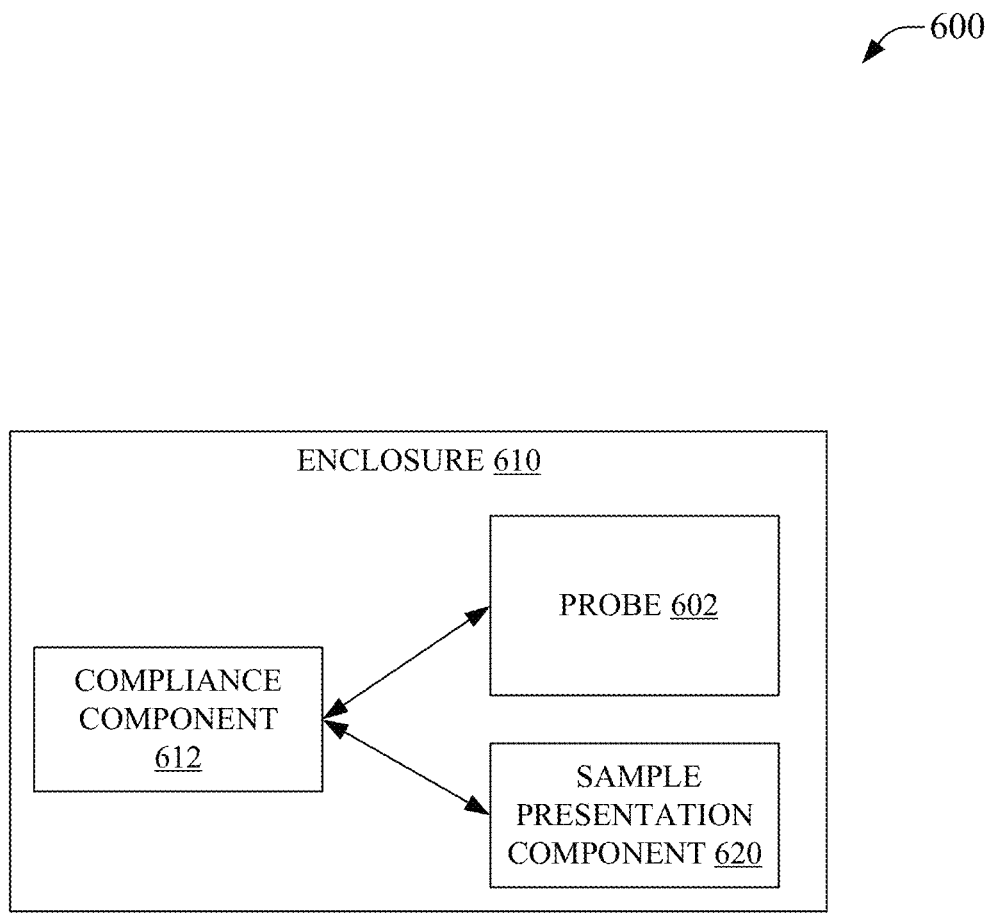
FIG. 6 is an illustration of an example system facilitating enclosing a sample to probe interface in accordance with aspects of the subject disclosure.

FIG. 6 is an illustration of a system 600, which facilitates enclosing a sample to probe interface in accordance with aspects of the subject disclosure. System 600 can include enclosure 610. Enclosure 610 can enclose an interface between a sample and a probe 602. In some embodiments, enclosure 610 can enclose probe 602 and sample presentation component 620. Probe 602 and sample presentation component 620 can be communicatively coupled to compliance component 612. In some embodiments, enclosure 610 can be a configured to rest on a surface, such as a table, bench, etc., as part of a benchtop analytical device, and may support probe 602 and sample presentation component 620, to allow an operator to open a portion of enclosure 610 to place a sample on sample presentation component 620 such that probe 602 can be used to analyze a sample within enclosure 610, e.g., enclosure 610 can be, or be part of, an enclosed benchtop Raman spectrometer, etc.

In some embodiments, probe 602 can include an interface for an analytical instrument to interrogate a sample, e.g., in a Raman spectrometer instrument, probe 602 can direct optical energy at a sample. In some embodiments, probe 602 can include an optical element, e.g., a lens, etc. that directs optical energy at a sample. In an example, the optical element of the probe 602 is configured to direct optical energy at a sample to facilitate non-contact-type optical interrogation of the sample from a distance, e.g., a focal point of the incident beam is a determined distance from the tip of the probe 602. For example, an aperture may be defined in a sample plate (which is an embodiment of the sample presentation component 620), and the probe 602 may be disposed within the aperture. A sample can be positioned on a topside of the sample plate over the location of the aperture. In this manner, the probe 602 is configured to direct optical energy at the sample from underneath the sample. In some configurations, even though the optical spectroscopy may not require the probe to contact the sample, the probe 602 may nevertheless be in contact with the sample (which, as mentioned herein, includes contact with the sample's package when the sample is contained in a transparent package) during optical spectroscopy of the sample. In an example configuration, the sample can be placed on the sample plate and held in place against the sample plate by the force of gravity and/or by sloped surface of, or a recessed area 425 defined in, the surface of the sample plate.

In some embodiments, the probe 602 may facilitate contact-type optical interrogation of a sample by a most distal portion of the probe 602 being in contact with the sample during optical interrogation. An example probe 602 that facilitates contact-type optical interrogation of a sample is a probe having a spherical lens. In an example, the spherical optical element (or lens) creates a focal point of the incident optical beam that is located at an interface between the spherical optical element and the sample where the sample contacts the most distal point of the probe 602. The spherical optical element can be a BallProbe® (MarqMetrix Inc., Seattle, Wash.). A BallProbe® can enable Raman spectrometry. In an aspect, a BallProbe® can allow for in-situ Raman spectrometry via probe 602. An example benchtop analytical device including a BallProbe® can perform Raman spectrometry by dipping or inserting the BallProbe® into a sample, against a sample, etc., and initiating an analytical interrogation of said sample.

In general, the probe 602 can facilitate analytical interrogation of the sample to excite atomic bonds of molecules in the sample such that a Raman spectrum can be captured, e.g., a response from sample interrogation. The Raman spectrum can then be analyzed. The analysis of the Raman spectrum can be based on reference Raman spectra. Of note, the terms 'spectrometry' and 'spectroscopy' are frequently used interchangeably in the art, though they can have slightly different connotations. The term 'spectrometry' is used in this disclosure in relation to the capture, analysis, and generation of results based on spectral information elicited via interrogation of a sample, as 'spectrometry' is believed to be the more correct term in this regard. However, the term 'spectrometry' is to be treated as inclusive of the common connotation of the term 'spectroscopy' as used by those of skill in the related art, unless otherwise explicitly indicated as having a narrower or different meaning in this disclosure.

In an aspect, embodiments of probe 602 can be constructed of nearly any material suitable to an expected sample environment. A probe can include a suitable polymer, e.g., polypropylene (PP), polyethylene terephthalate (PET), silicone, polytetrafluoroethylene (PTFE), etc. A probe can include other materials, such as, but not limited to, stainless steel, gold, or other metal; borosilicate or other glass; starches or other carbohydrates, etc.; or nearly any other material suitable to a particular sample environment. Moreover, materials can be machined, sintered, cast, injection molded, 3D-printed, etc., for example to form a body, optical element seat, shroud, etc., of a probe. Moreover, in some embodiments, an optical element can be 'spherical,' and can be separately manufactured and added to the body, either as part of a molding process, bonded with an adhesive, attached with a friction or press fit, mechanically captured, etc. In other embodiments, the 'spherical' optical element can be co-formed with the body as part of a molding process, e.g., the spherical optical element can be formed, of the same or a different material, with the removable optical assembly in injection molding; can be formed, of the same or a different material, with the removable optical assembly in 3D printing; etc. Additionally, 'spherical' optics can be manufactured from nearly any appropriate material, including the same or different materials as the body of a removable optical assembly. Non-limiting examples of appropriate materials can include a polymer, glass, mineral, etc., depending on the optical properties suited to a given scenario. Of note, the term 'spherical' optical element, or similar terms, as used herein, generally means an optical element, e.g., a lens, etc., that has a spherical, or nearly spherical, geometry. Moreover, the term 'spherical optical element,' as used herein, also includes any optical element that conducts light via a portion of the optical element that includes a curved surface approximating at least a portion of a sphere, for example, where sphere of optical glass has an shallow equatorial trench ground into it, such as to capture a retaining ring, etc., the resulting optical element, within the context of the instant disclosure, would still be considered a spherical optical element so long as light enters/exits the non-equatorial portions. As another example, an injection molded spherical optical element can include a protrusion, e.g., resembling a lollipop on a stick, and, within the context of the instant disclosure, would still be considered a spherical optical element. As a further example, an optical element including two individual hemispherical portions can also be considered a spherical element within the scope of the instant disclosure. It is to be appreciated that a lensing optical element of the probe 602 may be of a different shape than spherical, as described herein. For example, with non-contact-type optical interrogation of the sample from a distance, a non-spherical optical element (e.g., lens) may be utilized in the probe 602, such as a lens with a substantially flat surface at the distalmost point of the probe tip.

Sample presentation component 620 can include a sample retention portion that can retain a sample (e.g., the sloped surface and/or the recessed area 425 of the sample plates 420 shown in FIG. 4). In an aspect, sample presentation component 620 can include an adjustment mechanism allowing controlled motion of a sample stage or plate. In a further aspect, sample presentation component 620 can include a sensing component allowing for detection of interaction with a sample supported by a sample stage or plate. In another aspect, sample presentation component 620 can include a sample-arranging portion that allows placement of a sample for retention. As examples, sample presentation component 620 can be a liquid flow cell, a gas flow cell, a sample stage, a sample plate, etc. As other examples, sample presentation component 620 can be a sample stage or plate with a multi-well plate connector allowing a multi-well plate to be connected to the sample stage. This example sample stage or plate, in some embodiments can be connected to a translation component that can move the sample stage or plate, and thereby the multi-well plate relative to probe 602. This can enable sequential analysis of samples in one or more wells of the multi-well plate. In an aspect, a flow cell for either gas or liquid can be manifolded to enable handling of multiple gas/liquid streams, e.g., multiple sample inputs, reagent inputs, cleaning agent inputs, etc. The sample presentation component 620 may include a sample plate having an aperture defined therein, and a sloped surface or a recessed area around the aperture. A recessed area of the sample plate may be shaped to receive a sample package having a corresponding shape so that a sample can be interrogated through the package.

Enclosure 610 can provide optical separation between an operator and the interface between the sample and a probe. This can reduce the risk of an operator being exposed to optical energy that can escape from the interface area. Moreover, the enclosure 610 can reduce ambient light entering the interface, which can thereby reduce errors in analysis resulting from stray light reaching an optical detector of the benchtop instrument.

Compliance component 612 can be communicatively coupled to one or more of the enclosure 610, probe 602, and sample presentation component 620. Compliance component 612 can receive a compliance rule related to an aspect of system 600. Compliance component 612 can determine that the compliance rule has been satisfied. In an aspect, compliance component 612 can determine concurrent compliance with a group of compliance rules related to aspects of system 600. As an example, compliance component 612 can determine that an aspect of probe 602, and aspect of sample presentation component 620, and an aspect of enclosure 610 are concurrently compliant. As a more detailed example, probe 602 can be determined to be compliant based on determining than the attached probe is fit for a designated analysis profile, sample presentation component 620 can be determined to be compliant based on detecting that contact has been made with a sample on or in the sample presentation component 620, and enclosure 610 can be determined to be compliant based on output from a sensor associated with detecting when the enclosure 610 is closed, such that the compliance component can determine that, concurrently, the correct probe is on, the enclosure is closed, and the probe 602 has been put into contact with the sample of the sample presentation component 620. As another example, the sample presentation component 620 may be in the form of an exchangeable sample plate so that an operator can remove the sample plate from the enclosure 610 and replace it with another sample plate. The compliance component 612 can, in some embodiments, determine that the enclosure 610 is closed, and concurrently check for the presence of a sample presentation component 620 and/or that a sample is placed on or in the sample presentation component 620. In some embodiments, the compliance component 612 may determine whether a correct sample presentation component 620 is within the enclosure given an operator's input of a particular type of sample. For instance, exchangeable sample plates may have machine-readable codes that are read to determine whether the sample plate matches the package type input by an operator into the system 600. The compliance component 612 may additionally, or alternatively, determine, from a weight sensor, that a sample has been placed on the sample plate before allowing the analysis to proceed.

In some embodiments, compliance component 612 can enable access to data relating to determining compliance with one or more compliance rules, e.g., an operator can access information showing that the enclosure is not showing as 'closed,' a system including a processor can receive information indicating which probe is determined to be attached to probe 602, etc.

In another aspect, compliance component 612 can enable interrogation of the sample to proceed, e.g., release of optical energy to the sample can be in response to compliance component 612 determining that one or more rules of the group of compliance rules is (concurrently) satisfied. This aspect can reduce opportunities for release of laser energy, for example, where the enclosure is not properly closed, where the wrong probe is attached, where the probe is not in proper position/contact with the sample, etc. Moreover, this aspect can act as a trigger, such that as the compliance rules of the group of compliance rules progress towards contemporaneous compliance, the Raman spectrometer stands ready to interrogate the sample but cannot until the instant compliance component 612 determines that there is contemporaneous satisfaction of the compliance rules. In a further aspect, where one or more of the rules goes into non-compliance, compliance component 612 can determine that concurrent compliance is not occurring and can stop enabling release of optical energy, e.g., compliance component 612 can suspend or terminate the interrogation of a sample where any condition of system 600 represented by a compliance rule of the group of compliance rules transitions from satisfied to not satisfied. As an example, the emission of optical energy can be stopped where the enclosure is opened, where the probe is not in contact with the sample, etc.

Figure 7:
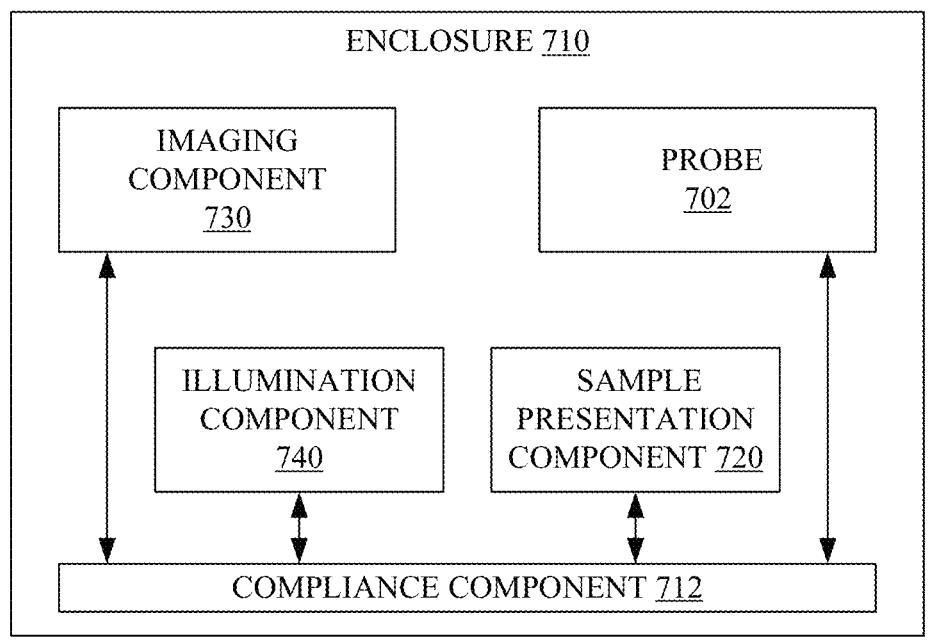
FIG. 7 is a depiction of an example system that facilitates indirect monitoring of a sample to probe interface for a benchtop analytical device including an enclosure in accordance with aspects of the subject disclosure.

FIG. 7 is a depiction of a system 700 that can facilitate indirect monitoring of a sample to probe interface for an optical analytical instrument including an enclosure in accordance with aspects of the subject disclosure. System 700 can include enclosure 710. Enclosure 710 can enclose an interface between a sample and an analytical instrument. In some embodiments, enclosure 710 can enclose probe 702 and sample presentation component 720. Probe 702 and sample presentation component 720 can be communicatively coupled to compliance component 712.

In some embodiments, probe 702 can include an optical element to direct optical energy at a sample. In some embodiments, the optical element that directs optical energy at a sample can include a spherical optical element. A spherical optical element can be a BallProbe® that can enable Raman spectrometry via probe 702. An example benchtop analytical device including probe 702 can perform Raman spectrometry by dipping or inserting a portion of probe 702 into a sample, against a sample, etc., and initiating an optical interrogation of said sample.

In some embodiments, sample presentation component 720 can present a sample for interrogation via probe 702. In an aspect, sample presentation component 720 can move relative to probe 702, e.g., in the x-axis, y-axis, z-axis, rotationally, etc., so as to be able to present different portions of a sample, different samples, etc., for analysis via probe 702. A position of sample presentation component 720 and probe 702 can be determined, e.g., via compliance component 712, via sample presentation component 720, via a connected controller/computer, etc. The positon can be employed to determine that the sample is appropriately oriented for optical interrogation. In an aspect, where a BallProbe® is employed, contact Raman spectroscopy can be performed, e.g., the spherical optical element can be placed directly against the sample, or in the sample, to interrogate the sample. In contact Raman, a position between probe 702 and the sample can be determined based on pressured applied between the probe 702 and the sample, e.g., as measured at the sample presentation component 720, etc., such that the BallProbe® can be brought into contact with the sample to perform the analysis, preferably without damage to the BallProbe® from the contact. In some embodiments, sample presentation component 720 can include a liquid flow cell, a gas flow cell, a sample stage, etc. In some example embodiments, sample presentation component 720 can include a sample plate. In some example embodiments, the sample presentation component 720 can include a multi-well plate, e.g., a 384-, 96-, 48-, 24-, 12-, 6-well plate sample container, etc. This can enable analysis of samples in one or more wells of the multi-well plate.

Enclosure 710 can provide optical separation between an operator and the interface between a sample and a probe 702. This can improve operator safety by blocking or attenuating optical emissions, e.g., scattered or reflected laser light, etc. Moreover, the enclosure can reduce ambient light entering the interface that can cause errors in the Raman analysis. In some embodiments, enclosure 710 can include optical attenuation features, e.g., paint and materials that absorb ambient light to reduce the effect of stray light reaching the detector during capture of a Raman spectrum.

Enclosure 710 can further enclose imaging component 730 and illumination component 740. Imaging component 730 and illumination component 740 can enable remote viewing of the interior of enclosure 710, more particularly a sample and the orientation of the sample and probe 702 as facilitated by positioning of the sample presentation component 720 and probe 702. In an aspect, imaging component 730 and illumination component 740 can illuminate and image the presentation of the sample to probe 702 in the human visible spectrum. In some embodiments, imaging component 730 and illumination component 740 can also illuminate and image the presentation of the sample to probe 702 in spectrum outside of the normal range of human vision, e.g., UV, IR, etc. Moreover, imaging component 730 and illumination component 740 can be communicatively coupled to compliance component 712. This can enable compliance component 712 to determine the state of imaging component 730 and illumination component 740 with regard to compliance rules for system 700. The imager/illuminator can enable an operator to position a probe 702 relative to a sample without needing to open the enclosure 710. In contrast to typical conventional benchtop Raman instruments, this can enable an operator to interrogate different portions of a sample by placing the sample in the enclosure, closing the enclosure, and then interacting with the sample interface via imaging and remote control of the sample stage or plate and/or Raman probe tip. As an example, where an inhomogeneous ore sample is placed in the enclosure, an analysis at a first location on the ore can provide a first result. The operator can then reposition the sample/probe to a second location via the imager to capture a second result. While this can appear trivial, there can be significant timesaving in enabling remote repositioning of the sample/probe rather than opening the enclosure to reposition a sample directly. Moreover, imaging and illumination can be done in spectral regions beyond human eyesight, e.g., IR, NIR, UV, etc., which can allow an operator to position a sample/probe relative to features that might not be visible to the human eye directly. As an example, a coral sample can include biological materials that fluoresce in UV light, allowing an operator to position the probe/sample via a UV sensitive imager and UV illuminator, then shutting off the UV illuminator to allow for Raman analysis at the selected location on the coral.

Compliance component 712 can be communicatively coupled to one or more of the enclosure 710, probe 702, sample presentation component 720, imaging component 730, illumination component 740, etc. Compliance component 712 can receive a compliance rule related to an aspect of system 700. Compliance component 712 can determine that the compliance rule has been satisfied. In an aspect, compliance component 712 can determine concurrent compliance with a group of compliance rules related to aspects of system 700. As an example, compliance component 712 can determine that the position of probe 702 relative to sample presentation component 720 is concurrently compliant with an illumination mode of illumination component 740, and that enclosure 710 is in an operable configuration. In response to determining that there is concurrent compliance among the set of compliance rules, in an aspect, compliance component 712 can enable release of optical energy for interrogation of the sample. This aspect can reduce opportunities for accidental release of laser energy, for example, where the enclosure is not properly closed, where the probe is not in proper position/contact with the sample, etc. Moreover, this aspect can act as a trigger, such that the compliance rules of the group define when an interrogation of the sample can begin. In another aspect, the compliance rules can benefit the analysis by determining the presence of conditions that are beneficial to improved operation of the Raman spectrometer, e.g., by determining that the illumination source is off before allowing the laser to fire on the sample, compliance component 712 removes ambient light in the enclosure that could interfere with the analysis. In a further aspect, compliance component 712 can disable the release of optical energy in response to determining that a rule has gone into non-compliance, e.g., compliance component 712 can determine that there is no longer concurrent compliance and, accordingly, can stop enabling release of optical energy.

Figure 8:
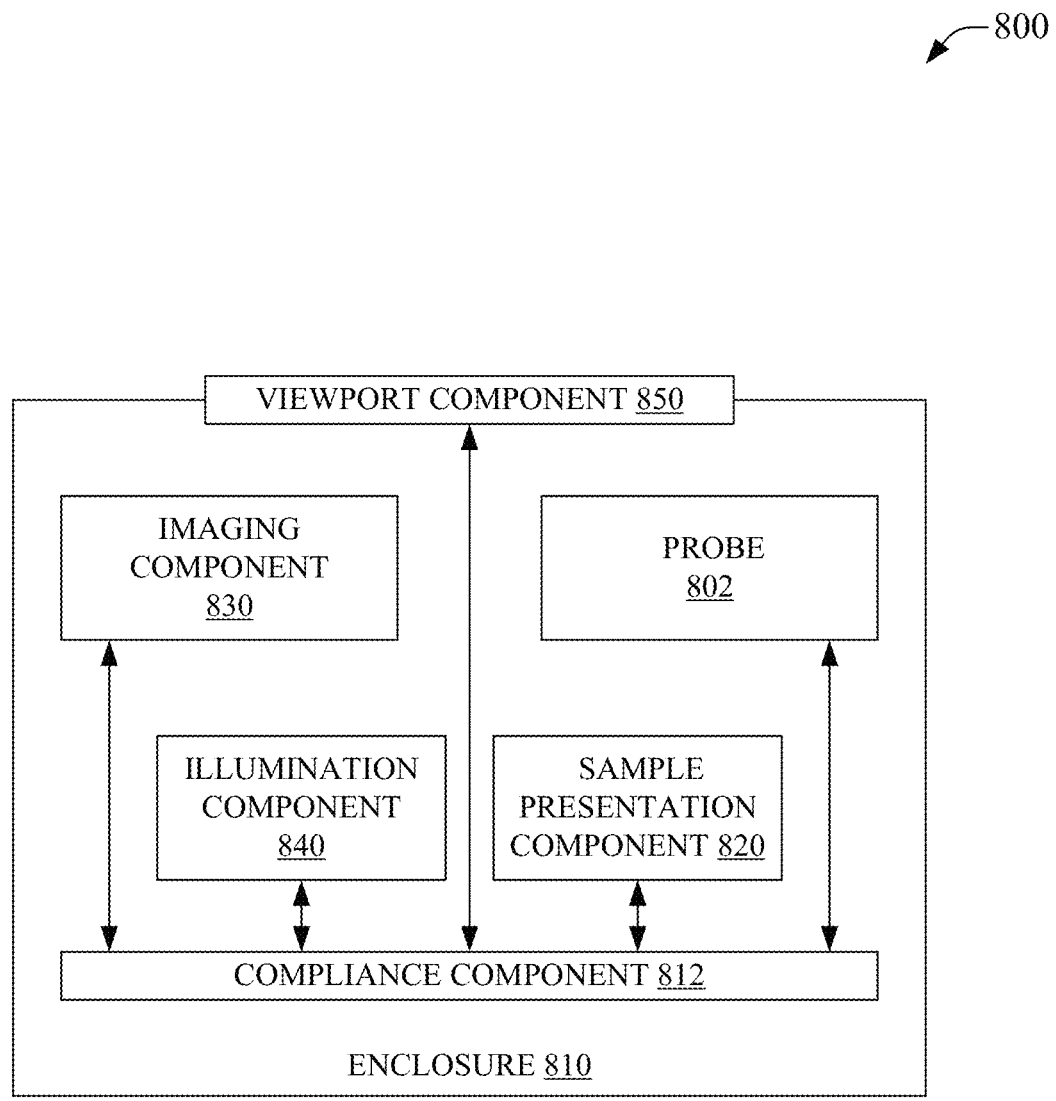
FIG. 8 illustrates an example system that facilitates direct monitoring of a sample to probe interface of a benchtop analytical device including an enclosure in accordance with aspects of the subject disclosure.

FIG. 8 illustrates a system 800 that facilitates direct monitoring of a sample to probe interface of an optical, benchtop analytical device including an enclosure in accordance with aspects of the subject disclosure. System 800 can include enclosure 810. Enclosure 810 can enclose an interface between a sample and a probe. In some embodiments, enclosure 810 can enclose probe 802, sample presentation component 820, imaging component 830, and illumination component 840. Probe 802, sample presentation component 820, imaging component 830, and illumination component 840 can be communicatively coupled to compliance component 812.

In some embodiments, probe 802 can include an optical element to direct optical energy at a sample. In some embodiments, the optical element that directs optical energy at a sample can include a spherical optical element. A spherical optical element can be a BallProbe® that can enable Raman spectrometry via probe 802. An example benchtop analytical device including probe 802 can perform Raman spectrometry by dipping or inserting a portion of probe 802 into a sample, against a sample, etc., and initiating an optical interrogation of said sample. In an aspect, probe 802 can move relative to sample presentation 820, e.g., in the x-axis, y-axis, z-axis, rotationally, etc., so as to be able to access different portions of a sample, different samples, etc., for analysis. Moreover, in some embodiments, motion of probe 802 can be in addition to, or in lieu of, motion by sample presentation component 820.

In some embodiments, sample presentation component 820 can present a sample for interrogation via probe 802. In an aspect, sample presentation component 820 can move relative to probe 802, e.g., in the x-axis, y-axis, z-axis, rotationally, etc., so as to be able to present different portions of a sample, different samples, etc., for analysis via probe 802. As previously noted, in some embodiments, motion of sample presentation component 820 can be in addition to, or in lieu of, motion by probe 802. A relative position between sample presentation component 820 and probe 802 can be determined, e.g., via compliance component 812, via sample presentation component 820, via a connected controller/computer, etc. The relative positon can be employed to determine that the sample is appropriately oriented for optical interrogation. In some embodiments, sample presentation component 820 can include a liquid flow cell, a gas flow cell, a sample stage, a sample plate, etc. In some example embodiments, sample presentation component 820 can include a multi-well plate, e.g., a 384-, 96-, 48-, 24-, 12-, 6-well plate sample container, etc. This can enable analysis of samples in one or more wells of the multi-well plate.

Imaging component 830 and illumination component 840 can enable remote viewing of the interior of enclosure 810, more particularly a sample and the orientation of the sample and probe 802 as facilitated by positioning of the sample presentation component 820 and probe 802. In an aspect, imaging component 830 and/or illumination component 840 can illuminate and/or image the presentation of the sample to probe 802 in the human visible spectrum. In some embodiments, imaging component 830 and illumination component 840 can also illuminate and image the presentation of the sample to probe 802 in spectrum outside of the normal range of human vision, e.g., UV, IR, etc. Moreover, imaging component 830 and illumination component 840 can be communicatively coupled to compliance component 812. This can enable compliance component 812 to determine the state of imaging component 830 and a state of illumination component 840 with regard to compliance rules for system 800.

Enclosure 810 can provide separation between the interior and exterior of enclosure 810, such that optical energy associated with interrogation of a sample is safely contained on the interior of enclosure 810, and that conditions external to enclosure 810 are less likely to interfere with the interrogation of the sample on the interior of enclosure 810. This can improve operator safety by blocking or attenuating optical emissions. Moreover, the enclosure 810 can reduce ambient light entering the interface that can cause errors in an optical interrogation of a sample. In some embodiments, enclosure 810 can include optical attenuation features, e.g., paint, materials, and structures that absorb or attenuate ambient light.

Enclosure 810 can include viewport component 850. Viewport component 850 can be communicatively coupled to compliance component 812. Viewport component 850 can include an opening in enclosure 810 that can allow for direct viewing into the interior of enclosure 810. In an aspect, the opening can include window materials to allow a direct view into the interior of enclosure 810 while maintaining the integrity of enclosure 810 with regard to other features, e.g., environmental control, venting, limiting release of laser light frequencies, etc. As an example, viewport component 850 can include a laser safe window to attenuate laser light that can escape the sample interface. As another example, viewport component 850 can include a shutter, sliding plate, etc., that can physically block light transmission. In this example, the operator can directly view the sample, for example to position it, then can provide an input, e.g., slide the shutter shut, press a start button, etc., that can cause the shutter to close before the analysis can proceed. Whereas compliance component 812 can enable the release of the laser energy when the shutter is closed, the action of shuttering can, in effect, also cause the laser to fire on the sample. Viewport component 850 can, in some embodiments, be employed in conjunction with imaging component 830, e.g., allowing for visualization in the visible spectrum via viewport component 850 and in the IR, UV, etc., spectrum via imaging component 830. In other embodiments, imaging component 830 can be excluded where viewport component 850 is included.

Compliance component 812 can be communicatively coupled to one or more of the enclosure 810, probe 802, sample presentation component 820, imaging component 830, illumination component 840, viewport component 850, etc. Compliance component 812 can receive a compliance rule related to an aspect of system 800. Compliance component 812 can determine that the compliance rule has been satisfied. In an aspect, compliance component 812 can determine concurrent compliance with a group of compliance rules related to aspects of system 800. As an example, compliance component 812 can determine that the position of probe 802 relative to sample presentation component 820 is concurrently compliant with a viewport component 850 indicating closed, and that enclosure 810 is in an operable configuration. In response to determining that there is concurrent compliance among the set of compliance rules, in an aspect, compliance component 812 can enable release of optical energy for interrogation of the sample. This aspect can reduce opportunities for accidental release of laser energy, for example, where viewport component 850 is not properly closed, where the probe is not in proper position/contact with the sample, etc. Moreover, this aspect can act as a trigger, such that the compliance rules of the group define when an interrogation of the sample can begin. In another aspect, the compliance rules can benefit the analysis by determining the presence of conditions that are beneficial to improved operation of the Raman spectrometer, e.g., by determining that the illumination source is off before allowing the laser to fire on the sample, compliance component 812 assures that ambient light in the enclosure has diminished. In a further aspect, compliance component 812 can disable the release of optical energy in response to determining that a rule has gone into non-compliance, e.g., compliance component 812 can determine that there is no longer concurrent compliance and, accordingly, can stop enabling release of optical energy.

Figure 9:
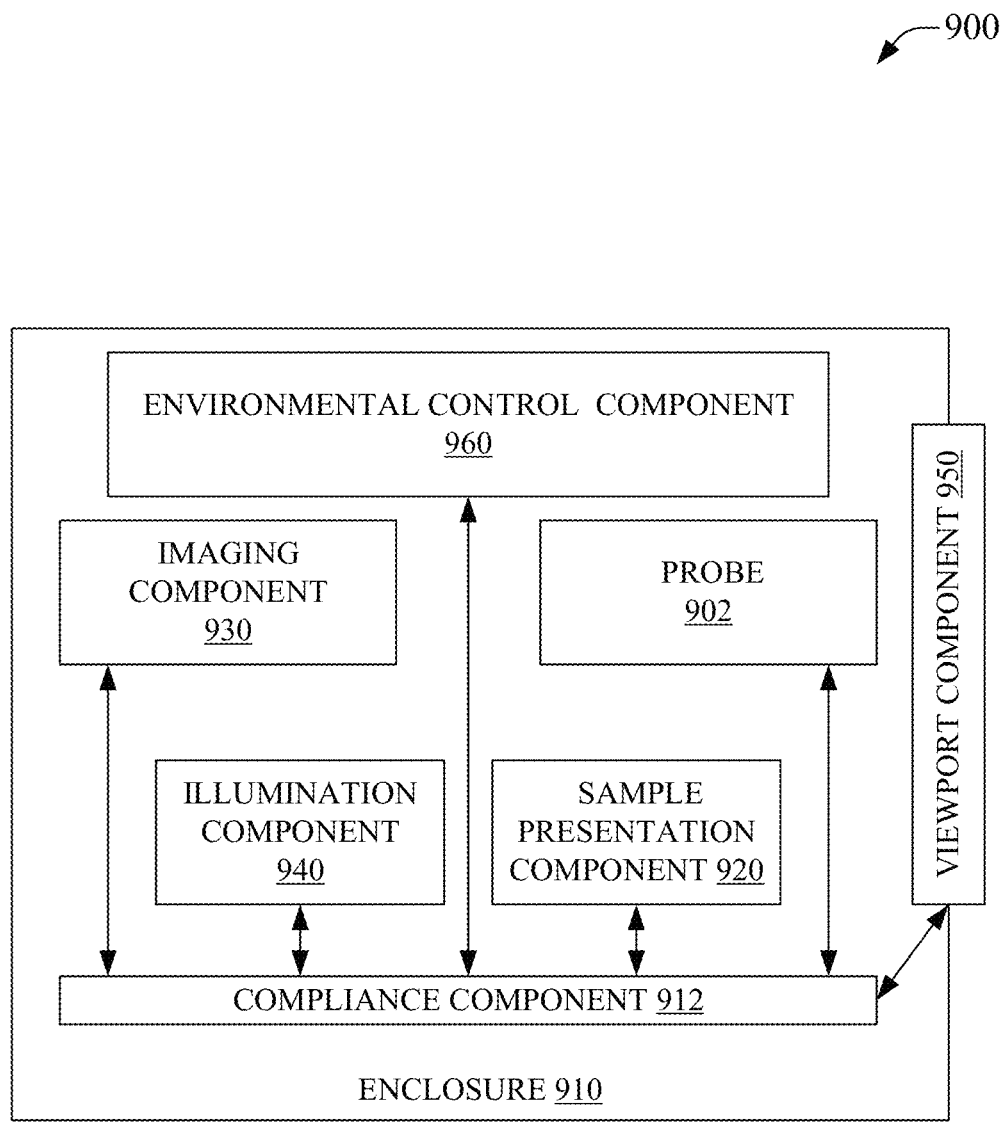
FIG. 9 illustrates an example system enabling environmental control within an enclosed benchtop analytical device in accordance with aspects of the subject disclosure.

FIG. 9 illustrates a system 900 enabling environmental control within an enclosed benchtop analytical device in accordance with aspects of the subject disclosure. System 900 can include enclosure 910. Enclosure 910 can enclose an interface between a sample and a probe 902. In some embodiments, enclosure 910 can enclose probe 902, sample presentation component 920, imaging component 930, and illumination component 940. Probe 902, sample presentation component 920, imaging component 930, and illumination component 940 can be communicatively coupled to compliance component 912.

In some embodiments, probe 902 can include an optical element to direct optical energy at a sample. In some embodiments, the optical element that directs optical energy at a sample can include a spherical optical element. A spherical optical element can be a BallProbe® that can enable Raman spectrometry via probe 902. An example benchtop analytical device including probe 902 can perform Raman spectrometry by dipping or inserting a portion of probe 902 into a sample, against a sample, etc., and initiating an optical interrogation of said sample. In an aspect, probe 902 can move relative to sample presentation component 920, e.g., in the x-axis, y-axis, z-axis, rotationally, etc., so as to be able to access different portions of a sample, different samples, etc., for analysis.

In some embodiments, sample presentation component 920 can present a sample for interrogation via probe 902. In an aspect, sample presentation component 920 can move relative to probe 902, e.g., in the x-axis, y-axis, z-axis, rotationally, etc., so as to be able to present different portions of a sample, different samples, etc., for analysis via probe 902. A position of sample presentation component 920 and probe 902 can be determined. The positon can be employed to determine that the sample is appropriately oriented for optical interrogation. In some embodiments, sample presentation component 920 can include a liquid flow cell, a gas flow cell, a sample stage, a sample plate, etc. In some example embodiments, sample presentation component 920 can include a multi-well plate. This can enable analysis of samples in one or more wells of the multi-well plate.

In some embodiments, system 900 can include environmental control component 960. Environmental control component 960 can enable control of an environment within enclosure 910. Environmental control component 960 can be communicatively coupled to compliance component 912. This can facilitate analysis of delicate samples, hazardous samples, etc. As an example, environmental control component 960 can maintain a temperature within enclosure 910, e.g., below freezing, to allow analysis of icy samples, at STP to allow analysis to be performed independent of temperature or pressure variation, etc. As another example, environmental control component 960 can vent the enclosure to a fume hood, scrubber or other filtration, etc., to enable analysis of volatile compounds. As a further example, environmental control component 960 can control humidity, for example to ramp humidity to illustrate a rate of absorption of water into a sample over time by monitoring the change in water in a sample as absorbed from the humidified air over time. In a still further example, environmental control component 960 can maintain a gaseous environment within enclosure 910, for example, an inert environment by filling the enclosure with helium, dry nitrogen, etc., a reactive environment by allowing a fixed amount of oxygen into the enclosure for an analysis of an oxidative event, etc., a reactive environment, etc. In addition, environmental component 960 can control aspects of other components of system 900, for example, controlling a hot-plate or cold-plate feature of sample presentation component 920, control of a stir-plate motion for a stir-plate enabled sample presentation component 920, control of illumination component 940 to, for example, UV sterilize the internal area of enclosure 910, etc.

Enclosure 910 can provide separation between the interior and exterior of enclosure 910, such that optical energy associated with interrogation of a sample is safely contained on the interior of enclosure 910, and that conditions external to enclosure 910 are less likely to interfere with the interrogation of the sample on the interior of enclosure 910. This can improve operator safety by blocking or attenuating optical emissions. Moreover, the enclosure can reduce ambient light entering the interface that can cause errors in an optical interrogation of a sample. In some embodiments, enclosure 910 can include optical attenuation features, e.g., paint, materials, and structures that absorb or attenuate ambient light.

Enclosure 910 can include viewport component 950. Viewport component 950 can be communicatively coupled to compliance component 912. Viewport component 950 can include an opening in enclosure 910 that can allow for direct viewing into the interior of enclosure 910. In an aspect, the opening can include window materials to allow a direct view into the interior of enclosure 910 while maintaining the integrity of enclosure 910 with regard to other features, e.g., environmental control, venting, limiting release of laser light frequencies, etc.

Enclosure 910 can further enclose imaging component 930 and illumination component 940. Imaging component 930 and illumination component 940 can enable remote viewing of the interior of enclosure 910, more particularly a sample and the orientation of the sample and probe 902 as facilitated by positioning of the sample presentation component 920 and probe 902. In an aspect, imaging component 930 and illumination component 940 can illuminate and image the presentation of the sample to probe 902 in the human visible spectrum. In some embodiments, imaging component 930 and illumination component 940 can also illuminate and image the presentation of the sample to probe 902 in spectrum outside of the normal range of human vision, e.g., UV, IR, etc. Moreover, imaging component 930 and illumination component 940 can be communicatively coupled to compliance component 912. This can enable compliance component 912 to determine the state of imaging component 930 and illumination component 940 with regard to compliance rules for system 900. In some embodiments, illumination component 940 can further enable sterilization within enclosure 910, e.g., illumination component 940 can generate sufficient UV radiation to sterilize some, or all, of the interior of enclosure 910, etc. In some embodiments, a UV sterilization feature can be controlled by environmental control component 960.

Compliance component 912 can be communicatively coupled to one or more of the enclosure 910, probe 902, sample presentation component 920, imaging component 930, illumination component 940, viewport component 950, environmental control component 960, etc. Compliance component 912 can receive a compliance rule related to an aspect of system 900. Compliance component 912 can determine that the compliance rule has been satisfied. In an aspect, compliance component 912 can determine concurrent compliance with a group of compliance rules related to aspects of system 900. As an example, compliance component 912 can determine that the position of probe 902 relative to sample presentation component 920 is concurrently compliant with an illumination mode of illumination component 940, an internal inter gas environment via environmental control component 960, and that enclosure 910 is in an operable (e.g., closed) configuration. In response to determining that there is concurrent compliance among the set of compliance rules, in an aspect, compliance component 912 can enable release of optical energy for interrogation of the sample. This aspect can reduce opportunities for accidental release of laser energy, for example, where the enclosure is not properly closed, where the probe is not in proper position/contact with the sample, etc. Moreover, this aspect can act as a trigger, such that the compliance rules of the group can define when an interrogation of the sample can begin. In another aspect, the compliance rules can benefit the analysis by determining the presence of conditions that are beneficial to improved operation of the Raman spectrometer. As an example, by determining that the illumination source is off before allowing the laser to fire on the sample, compliance component 912 removes ambient light in the enclosure that could interfere with the analysis. As another example, by determining that the sample is in a stable predetermined temperature, via environmental control component 960, the captured spectral data can be more consistent than for data captured at varying temperatures. In a further aspect, compliance component 912 can disable the release of optical energy in response to determining that a rule has gone into non-compliance, e.g., compliance component 912 can determine that there is no longer concurrent compliance and, accordingly, can stop enabling release of optical energy.

Figure 10:
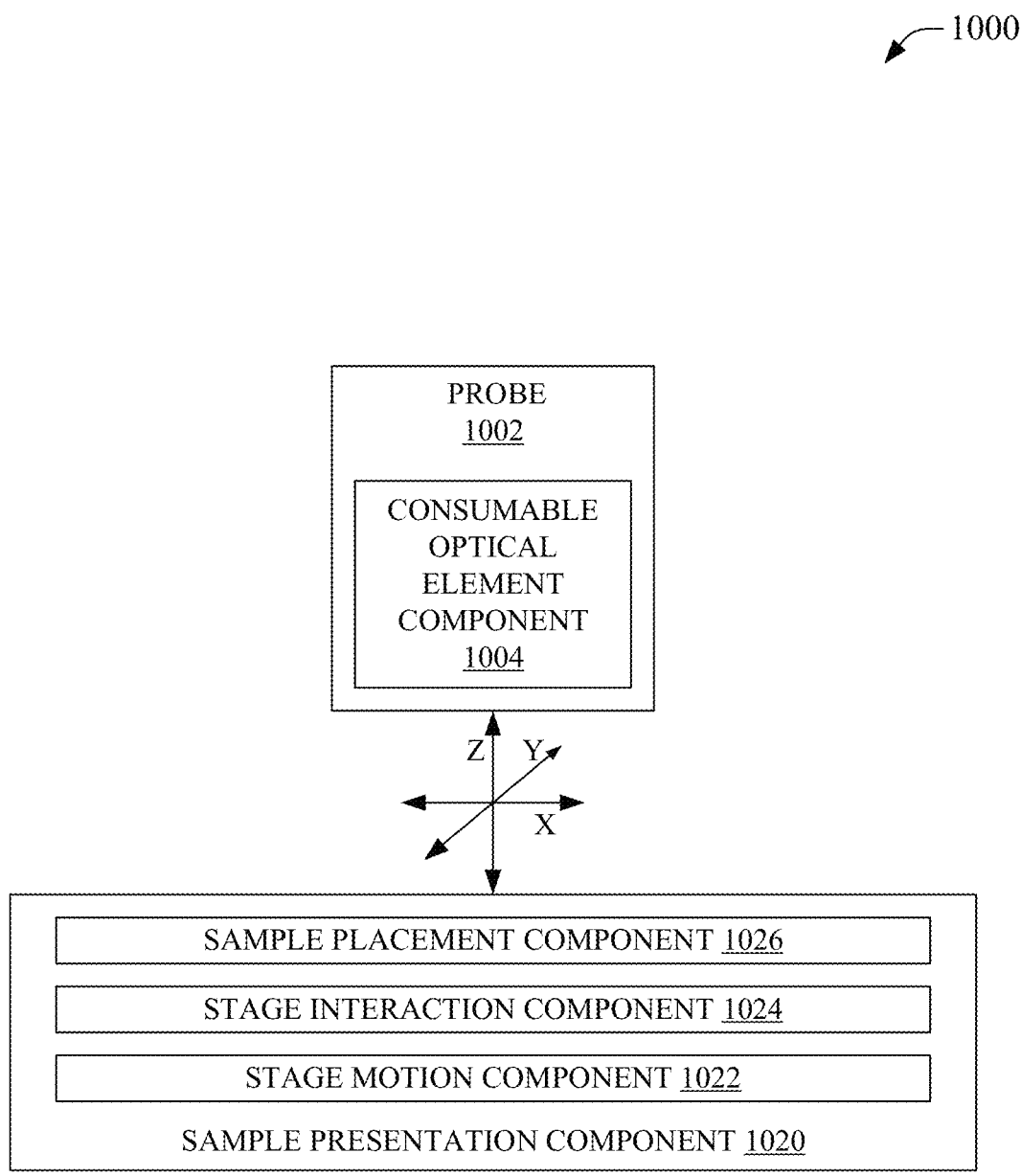
FIG. 10 illustrates an example system that facilitates translation of a sample stage for an enclosed benchtop analytical device in accordance with aspects of the subject disclosure.

FIG. 10 illustrates a system 1000 that facilitates translation of a sample stage for an enclosed benchtop analytical device in accordance with aspects of the subject disclosure. System 1000 can include probe 1002 and sample presentation component 1020. Probe 1002 and sample presentation component 1020 can move relative to each other, e.g., in the x-, y-, and z-planes, rotationally, etc. This can allow a sample to be positioned relative to probe 1002 to enable optical analysis, e.g., Raman spectroscopy, IR spectroscopy, UV-Vis spectroscopy, etc., at determined locations of the sample. In another aspect, where sample presentation component 1020 includes a plurality of samples, these samples can be positioned relative to probe 1002 to enable optical analysis of one or more of the plurality of samples.

In some embodiments, probe 1002 can include an optical element to direct optical energy at a sample. In some embodiments, the optical element that directs optical energy at a sample can include a spherical optical element. A spherical optical element can be a BallProbe® that can enable Raman spectrometry via probe 1002. An example benchtop analytical device including probe 1002 can perform Raman spectrometry by dipping or inserting a portion of probe 1002 into a sample, against a sample, etc., and initiating an optical interrogation of said sample. In an aspect, probe 1002 can move relative to sample presentation component 1020, e.g., in the x-axis, y-axis, z-axis, rotationally, etc., so as to be able to access different portions of a sample, different samples, etc., for analysis.

In some embodiments, the probe tip can be consumable or exchangeable. This can be in lieu of, or in addition to, the probe tip being cleanable. It will be appreciated that repeated use of a probe tip without cleaning can result in changes to the condition of the probe tip that can alter captured results. As an example, contact of a probe tip with tar can result in the tar adhering to an optical element of the probe and preventing accurate results in following analytical runs of the instrument. In these situations, the tip can be cleaned or exchanged. In an aspect, this can occur in the enclosure. Moreover, some samples can be affiliated with particular types of tips, for example, sampling of concentrated hydrofluoric acid can be better performed with a plastic lens probe tip than a glass lens probe tip. As another example, a first depth of focus can be desired for a first analysis and a different second depth of focus can be desired for another analysis. The disclosed subject matter can include a cleaning component to enable cleaning of a probe tip. Moreover, the disclosed subject matter can include a plurality of other probe tips to allow for replacement of consumed probe tips, exchange of tips suited to an analysis, etc. As an example, a probe tip dipped in tar can be moved to the cleaning component and a different probe tip can be substituted. This can allow the analysis to continue while the first tip is being cleaned. In another example, a damaged tip can be disposed of and a replacement tip can be retrieved from the battery of tips. In a further example, a first tip can be used for a first analysis and then a second tip can be used for a second analysis without needing to open the enclosure. Moreover, the compliance component can, in some embodiments, check the condition of a probe tip to determine if replacement of the tip should occur, e.g., a self-diagnostic, calibration, etc.

Accordingly, in some embodiments, probe 1002 can include consumable optical element component 1004. In an aspect, consumable optical element component 1004 can include the optical element to direct optical energy at the sample. As an example, consumable optical element component 1004 can be a disposable tip with a spherical optical element that is connected to probe 1002. As such, when consumable optical element component 1004 becomes dirty, damaged, ill suited to the determined optical analysis, etc., consumable optical element component 1004 can be jettisoned and a replacement consumable optical element component 1004 can be connected to probe 1002 to proceed with further analysis. As an example, disposable pipette tips can be analogous to consumable optical element component 1004, in that as much as a disposable pipette tip can be used repeatedly, there are situations in which replacement of the disposable pipette tip is desirable, e.g., to prevent cross contamination, damage to the tip, fouling of the tip, etc. Similarly, consumable optical element component 1004 can allow continued use of an optical element until it is determined that the consumable optical element component 1004 should be replaced with another consumable optical element component 1004. In an aspect, the replacement consumable optical element component 1004 can be the same, similar to, or different from, the consumable optical element component 1004 being replaced.

Moreover, in some embodiments, consumable optical element component 1004 can be constructed of nearly any material. Consumable optical element component 1004 can include a suitable polymer. Consumable optical element component 1004 can include other materials, such as, but not limited to, stainless steel, gold, or other metal; borosilicate or other glass; starches or other carbohydrates, etc.; or nearly any other material suitable to a particular sample environment. Moreover, materials can be machined, sintered, cast, injection molded, 3D-printed, etc., for example to form a body, optical element seat, shroud, etc., of consumable optical element component 1004. As an example, consumable optical element component 1004 can include a polymer body having a sufficiently high coefficient of friction to allow it to be retained by a friction press fit on a receiving end of probe 1002. In another aspect, some embodiments of consumable optical element component 1004 can include an optical element that can be generally spherical. The optical element can be separately manufactured and added to the body of consumable optical element component 1004, either as part of a molding process, bonded with an adhesive, attached with a friction or press fit, mechanically captured, etc. In other embodiments, the spherical optical element can be co-formed with the body as part of a molding process, e.g., the spherical optical element can be formed, of the same or a different material, as the consumable optical element component 1004 body, such as by injection molding; can be formed, of the same or a different material, as the consumable optical element component 1004 via 3D printing; etc. Additionally, spherical optical elements can be manufactured from nearly any appropriate material, including the same or different materials as the body of consumable optical element component 1004. Non-limiting examples of appropriate materials can include a polymer, glass, mineral, etc., depending on the optical properties suited to a given scenario. As noted herein above, 'spherical' optical element, or similar terms, can refer to an optical element, e.g., a lens, etc., that has a spherical, or nearly spherical, geometry. Moreover, the term 'spherical optical element,' as used herein, can also include any optical element that conducts light via a portion of an optical element that includes a curved surface approximating at least a portion of a sphere. As an example, an optical element including two individual generally hemispherical portions can also be considered a spherical element within the scope of the instant disclosure.

In some embodiments, sample presentation component 1020 can present a sample for interrogation via probe 1002. In an aspect, sample presentation component 1020 can move relative to probe 1002, e.g., in the x-axis, y-axis, z-axis, rotationally, etc., so as to be able to present different portions of a sample, different samples, etc., for analysis via probe 1002. A position of sample presentation component 1020 and probe 1002 can be determined. The positon can be employed to determine that the sample is appropriately oriented for optical interrogation. In some embodiments, sample presentation component 1020 can include a liquid flow cell, a gas flow cell, a sample stage, a sample plate, etc. In some example embodiments, sample presentation component 1020 can include a multi-well plate. This can enable analysis of samples in one or more wells of the multi-well plate.

Movement of sample presentation component 1020 can be enabled by stage motion component 1022. In an aspect, stage motion component 1022 can include, for example, servo motors, piezo-electric actuators, etc., allowing movement of sample placement component 1026. Sample placement component 1026 can facilitate positioning of a sample in a location that can be treated as static in regard to a reference point of sample presentation component 1020, such that motion of sample presentation component 1020 can be correlated with motion of the sample positioned by sample placement component 1026. In an aspect, sample placement component 1026 can include a multi-well plate, a flow cell for a gas and/or liquid, mechanical gripper assembly, an adhesive, a suction gripper assembly, etc., allowing for placement of a sample that is in at least one of a solid, liquid, or gas phase, such that sample presentation component 1020 can present the sample to probe 1002 for optical analysis. As an example, a chunk of rock can be adhered to a sample stage, e.g., sample placement component 1026, via a piece of double sided tape, allowing stage motion component 1022 to move the rock into position relative to the position/movement of probe 1002 to enable a spherical optic of consumable optical element 1004 to pass laser light onto a desired portion of the rock for Raman analysis thereof. Moreover, sample presentation component 1020 can include stage interaction component 1024 that can determine interaction between the probe 1002 and the sample. In an aspect, stage interaction component 1024 can determine when probe 1002 comes into contact with a sample, is located at a determined distance into a sample, e.g., a liquid or gas sample into which probe 1002 is dipped, etc., is at a determined angle to the sample, etc. As an example, where a BallProbe® equipped consumable optical element component 1004 is used for contact Raman analysis, the BallProbe® tip can be brought into physical contact with the sample. Stage interaction component 1024 can determine when contact has occurred. This determined contact can be employed by a compliance component, e.g., 612, 712, 812, 912, etc., to aid in determining concurrent satisfaction of compliance rules. Moreover, this determined contact can be employed to stop additional motion between probe 1002 and sample presentation component 1020 that could damage the BallProbe® optical element, e.g., crushing it via additional pressure, scratching it by lateral motion while the BallProbe® is in contact with a solid sample, etc. As an example, a spring-biased pressure sensor can determine contact has been made without exceeding the bias pressure exerted by the bias spring. As another example, an ultrasonic proximity sensor can be employed to determine a distance between the sample presentation component 1020 and probe 1002, which can be used with a model to determine a distance of the probe tip to/into the sample. Numerous other examples are readily appreciated by one of skill in the art and all such examples are within the scope of the present disclosure despite not being explicitly recited for the sake of clarity and brevity.

Figure 11:
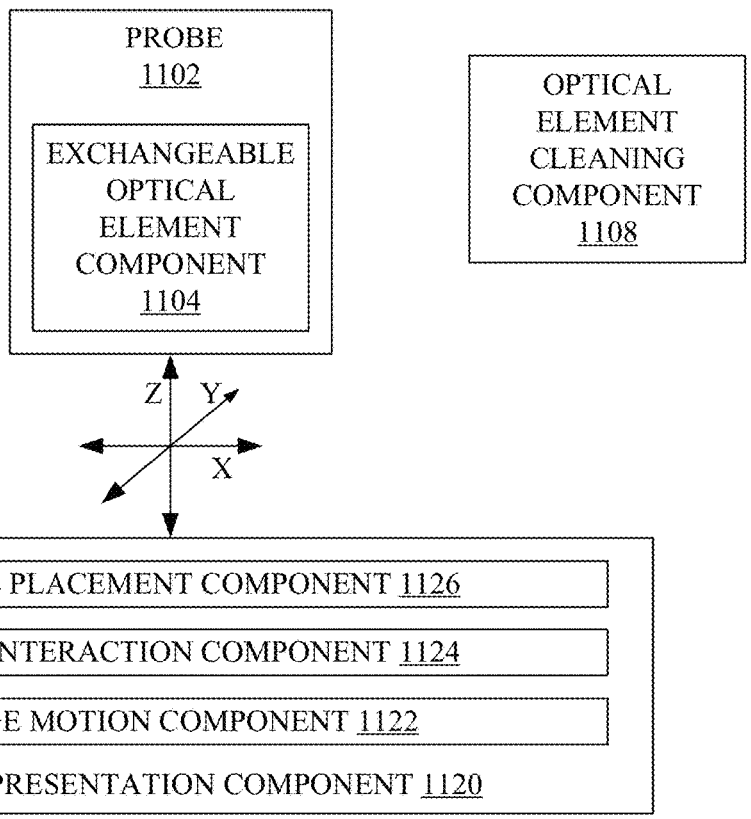
FIG. 11 illustrates an example system enabling cleaning or replacement of an exchangeable optical element component of a probe for an enclosed benchtop analytical device in accordance with aspects of the subject disclosure.

FIG. 11 illustrates a system 1100 that facilitates cleaning or replacement of an exchangeable optical element component of a probe for an enclosed benchtop analytical device in accordance with aspects of the subject disclosure. System 1100 can include probe 1102 and sample presentation component 1120. Probe 1102 and sample presentation component 1120 can move relative to each other, e.g., in the x-, y-, and z-planes, rotationally, etc. This can allow a sample to be positioned relative to probe 1102 to enable optical analysis at determined locations of the sample. In another aspect, where sample presentation component 1120 includes a plurality of samples, these samples can be positioned relative to probe 1102 to enable optical analysis of one or more of the plurality of samples.

In some embodiments, probe 1102 can include an optical element to direct optical energy at a sample. In some embodiments, the optical element that directs optical energy at a sample can include a spherical optical element. A spherical optical element can be a BallProbe® that can enable Raman spectrometry via probe 1102. An example benchtop analytical device including probe 1102 can perform Raman spectrometry by dipping or inserting a portion of probe 1102 into a sample, against a sample, etc., and initiating an optical interrogation of said sample. In an aspect, probe 1102 can move relative to sample presentation 1120, e.g., in the x-axis, y-axis, z-axis, rotationally, etc., so as to be able to access different portions of a sample, different samples, etc., for analysis.

In some embodiments, probe 1102 can include exchangeable optical element component 1104. In an aspect, exchangeable optical element component 1104 can include the optical element to direct optical energy at the sample. As an example, exchangeable optical element component 1104 can be an exchangeable tip with a spherical optical element that is connected to probe 1102. As such, when exchangeable optical element component 1104 becomes dirty, damaged, ill suited to the determined optical analysis, etc., a first exchangeable optical element component 1104 can be removed and a second exchangeable optical element component 1104 can be attached to probe 1102 to proceed with further analysis.

In an aspect, this can enable different exchangeable optical element components to be rotated into use based on the characteristics of the several exchangeable optical element components. As an example, a first exchangeable optical element component can have a sapphire lens and a second exchangeable optical element component can have a plastic lens. The second exchangeable optical element component can be used in conditions that do not require the sapphire lens of the first exchangeable optical element component, e.g., because damage to the plastic lens is less costly than to the sapphire lens), however, where an analysis is determined to be better suited to use of the sapphire lens, the second exchangeable optical element component can be exchanged for the first exchangeable optical element component. After the analysis with the sapphire lens is performed, the first exchangeable optical element component can be re-exchanged for the second exchangeable optical element component.

Moreover, in some embodiments, system 1100 can include exchangeable optical element component storage 1106 (e.g., a container). Exchangeable optical element component storage 1106 can store exchangeable optical element component(s) that can be exchanged for exchangeable optical element component 1104. In an aspect, exchangeable optical element component storage 1106 can store a supply of disposable or consumable optical element components. In another aspect, exchangeable optical element component storage 1106 can store other exchangeable optical element components. As an example, a modern computer numerical control (CNC) milling machine can be equipped with a turret system allowing rapid and automated exchange of milling machining tools, similarly, exchangeable optical element component storage 1106 can allow for the rapid and automated exchange of exchangeable optical element components within an enclosure, e.g., 110, 310, 610-910, etc.

In some embodiments, probe 1102 can employ optical element cleaning component 1108 to clean optical elements of probe 1102. In some embodiments, optical element cleaning component 1108 can validate that the optical element of probe 1102 is clean, e.g., via calibration, intensity correction, flat-fielding techniques, wavelength registration techniques, etc. As an example, optical element cleaning component 1108 can sonicate a probe tip dipped in a solvent between analytical runs where Raman spectra is being taken on oil samples, which can rinse the oil from the probe tip, e.g., the optical element in contact with the oil can be cleaned, to allow an exchangeable optical element component 1104 to be reused. The cleanliness of the optical element can be verified before reuse. Where the cleanliness of the optical element fails, the optical element can be re-cleaned and validated or, in some embodiments, exchanged for a replacement exchangeable optical element component 1104.

In some embodiments, exchangeable optical element component 1104 can be constructed of nearly any material. Exchangeable optical element component 1104 can include a suitable polymer. Exchangeable optical element component 1104 can include other materials, such as, but not limited to, stainless steel, gold, or other metal; borosilicate or other glass; starches or other carbohydrates, etc.; or nearly any other material suitable to a particular sample environment. Moreover, materials can be machined, sintered, cast, injection molded, 3D-printed, etc., for example to form a body, optical element seat, shroud, etc., of exchangeable optical element component 1104. In another aspect, some embodiments of exchangeable optical element component 1104 can include an optical element that can be generally spherical. Additionally, spherical optical elements can be manufactured from nearly any appropriate material, including the same or different materials as the body of exchangeable optical element component 1104. As noted herein above, spherical optical element, or similar terms, can refer to an optical element, e.g., a lens, etc., that has a spherical, or nearly spherical, geometry. Moreover, the term spherical optical element, as used herein, can also include any optical element that conducts light via a portion of an optical element that includes a curved surface approximating at least a portion of a sphere.

In some embodiments, sample presentation component 1120 can present a sample for interrogation via probe 1102. In an aspect, sample presentation component 1120 can move relative to probe 1102, e.g., in the x-axis, y-axis, z-axis, rotationally, etc., so as to be able to present different portions of a sample, different samples, etc., for analysis via probe 1102. A position of sample presentation component 1120 and probe 1102 can be determined. The positon can be employed to determine that the sample is appropriately oriented for optical interrogation. In some embodiments, sample presentation component 1120 can include a liquid flow cell, a gas flow cell, a sample stage, a sample plate, etc. In some example embodiments, sample presentation component 1120 can include a multi-well plate. This can enable analysis of samples in one or more wells of the multi-well plate.

Movement of sample presentation component 1120 can be enabled by stage motion comp 1122. In an aspect, stage motion comp 1122 can allowing movement of sample placement component 1126. Sample placement component 1126 can facilitate positioning of a sample in a location that can be treated as static in regard to a reference point of sample presentation component 1120, such that motion of sample presentation component 1120 can be correlated with motion of the sample positioned by sample placement component 1126.

Moreover, sample presentation component 1120 can include stage interaction component 1124 that can determine interaction between the probe 1102 and the sample. In an aspect, stage interaction component 1124 can determine when probe 1102 comes into contact with a sample, is located at a determined distance into a sample, e.g., a liquid or gas sample into which probe 1102 is dipped, etc., is at a determined angle to the sample, etc. This determined interaction can be employed by a compliance component, e.g., 612, 712, 812, 912, etc., to aid in determining concurrent satisfaction of compliance rules. Moreover, this determined interaction can be employed to stop additional motion between probe 1102 and sample presentation component 1120.

Figure 12:
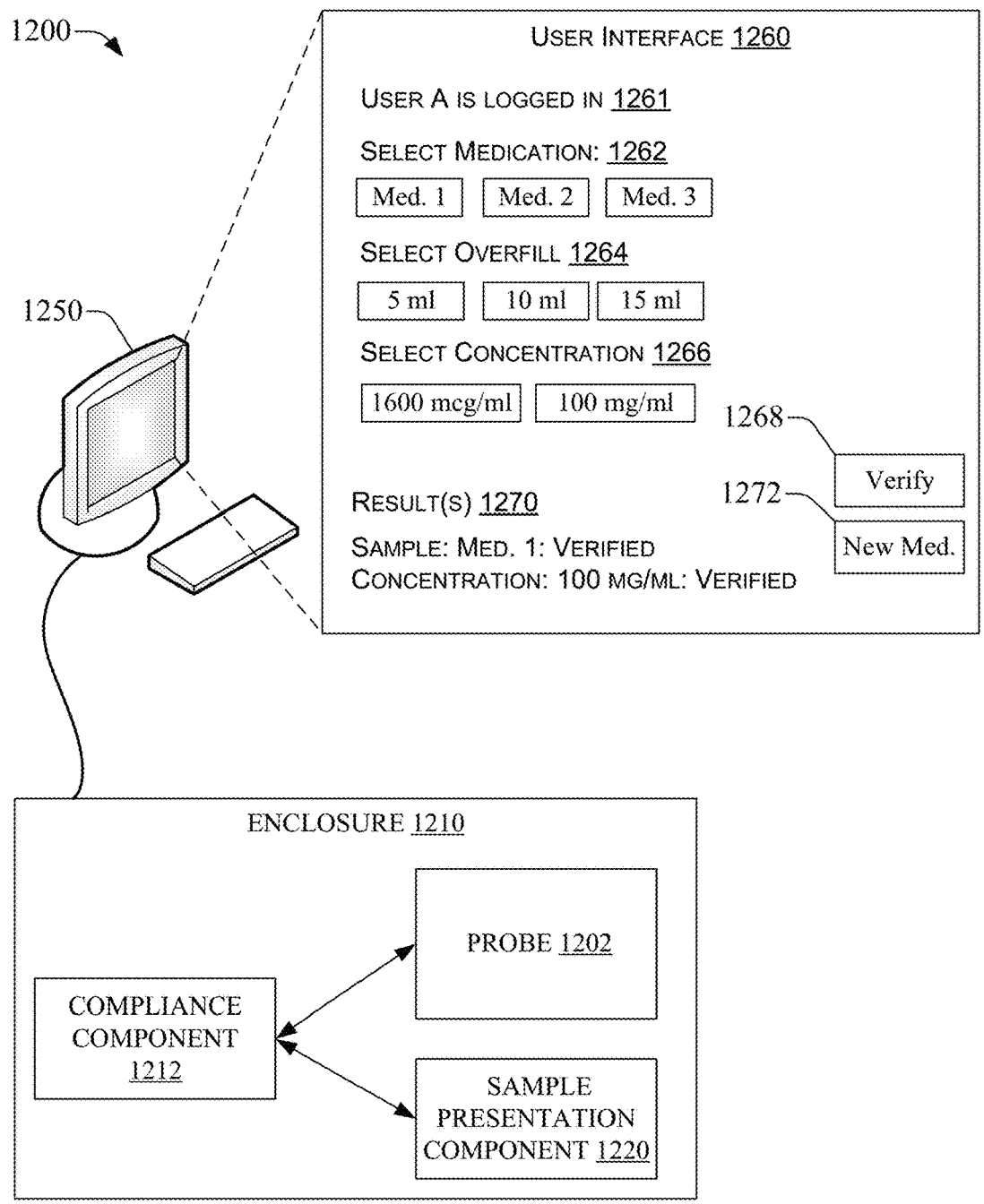
FIG. 12 illustrates an example system including an enclosure of a benchtop analytical device and a computer coupled thereto for providing a user interface for operational control of the system and for viewing analysis results in accordance with aspects of the subject disclosure.

FIG. 12 illustrates an example system 1200 including an enclosure 1210 and a computer 1250 (with a display) coupled thereto for providing a user interface 1260 for operational control of the system 1200 and viewing analysis results in accordance with aspects of the subject disclosure. As described herein, the enclosure 1210 may include at least a probe 1202, a sample presentation component 1220, and a compliance component 1212 for performing optical spectroscopy of a sample within the enclosure.

An operator may interact with the computer 1250 coupled (via wired or wireless communication) to the enclosure 1210 using one or more input devices (e.g., mouse, keyboard, touchscreen, etc.), and the display of the computer 1250 may provide a user interface 1260, as shown in FIG. 12. An operator may power on the system 1200, place a sample within the enclosure 1210 so that the sample and the probe 1202 are positioned to allow the probe 1202 to optically interrogate the sample during optical spectroscopy. The operator may close the lid of the enclosure 1210, and may start interacting with the user interface 1260. The compliance 1212 component may ensure that one or more compliance rules are satisfied (e.g., the enclosure 1210 is closed) before optical spectroscopy can be performed within the enclosure 1210.

The user interface 1260 may indicate, at 1261, that a particular user is logged into a user account maintained by the system 1200. This may be accomplished by any suitable technique, such as the operator providing credentials (e.g., a username and a password), biometric (e.g., fingerprint, iris scan, voice recognition, etc.) identification, or any other suitable technique to identify the operator. By associating the operator/user with a particular analysis, statistics can be collected on individual operators to determine if they are compliant with procedures and/or protocols, and the like. Furthermore, a compliance rule (used by the compliance component) may relate to determining that an operator of the benchtop analytical device has logged into a user account. Accordingly, the compliance component may not enable emission of optical energy via the probe 1202 unless and until this rule is satisfied (e.g., unless and until an operator logs into a user account).

The user interface 1260 may present a first section 1262 for the operator to select one of multiple available types of samples. In the example of FIG. 12, the sample types are in the form of multiple available types of medications (or pharmaceuticals), but the system 1200 can be configured to analyze any type of sample and is not limited to medications. For instance, the system 1200 may maintain a database of multiple types of food, or any other type of sample. In any case, the example of FIG. 12 shows three medications, but it is to be appreciated that the system 1200 may maintain a database of any suitable number of different sample types (e.g., types of medications) that can be selected by the operator for purposes of verifying the type of sample and/or the concentration of the sample. In an example, the operator may select medication 1 in the select medication section 1262, which may correspond to a drug such as Cefazolin, which is an antibiotic.

The user interface 1260 may additionally, or subsequent to selection of a sample type (e.g., a type of medication), present a second section 1264 for the operator to select an overfill amount of the sample (e.g., medication), such as an amount of overfill in milliliters (ml). In an example, the operator may select an overfill of 10 ml. Depending on the type of sample analyzed, the overfill section 1264 may be omitted if it is not applicable to the type or category of sample.

The user interface 1260 may additionally, or subsequent to selection of a medication and an overfill amount, present a third section 1266 for the operator to select a concentration of the sample (e.g., medication), such as a concentration in micrograms (mcg) per ml, or milligrams (mg) per ml. In an example, the operator may select a concentration of 100 mg/ml. In some embodiments, the selection of a sample type in the first section 1262 may cause other parameters in the other sections to auto-populate with known values for the selected sample type. For example, the database of sample types may include a single predefined concentration for a particular sample type (e.g., fentanyl). In this example, the operator may select the desired sample type in the first section 1262, and the remaining parameter(s) (e.g., concentration) may auto-populate with known values, such as a single predefined concentration specified in the database for that sample type. This can simplify the user interface for the operator by allowing the operator to perform optical spectroscopy on a sample with merely a selection of one or two buttons in the user interface 1260.

With a sample (e.g., medication), an overfill amount, and a concentration selected, the operator may select a verify button 1268 (e.g., or a start button implemented as a soft button on the user interface 1260). Upon selection of the verify button 1268, optical spectroscopy of the sample may be performed via the probe 1202 within the enclosure 1210, and one or more results of the analysis may be presented on in a results section 1270 of the user interface 1260. The results section 1270 may indicate whether the type of sample (such as a type of medication) is verified via optical spectroscopy (e.g., by determining that the obtained Raman spectra matches a known Raman spectra of the type of sample), and/or whether the concentration of the sample is verified via optical spectroscopy (e.g., using an algorithm that is a function of the intensity of the obtained Raman spectra). In the running example, the system 1200 has verified that the sample placed within the enclosure 1210 is indeed the medication selected by the operator (e.g., Medication 1: Cefazolin), and is indeed at the concentration selected by the operator (e.g., 100 mg/ml). If the sample was not verified to be the type of sample selected by the operator, the results section 1270 may indicate as much by a different output, such as "not verified." Although the various sections 1262, 1264, 1266, 1270 are shown in a single user interface 1260, it is to be appreciated that these sections may be presented in a series of sequential user interfaces.

If the operator would like to verify additional samples of the same type, overfill, and concentration selected for the first sample, the system 1200 can maintain the selections of the operator and the operator may simply open the lid of the enclosure 1210, replace the previously-analyzed sample with another sample that is suspected to be the same type of sample (in the same amount of overfill and the same concentration), close the lid of the enclosure 1210, and select the verify button 1268 for the next sample. This allows an operator to perform batch processing to verify multiple samples (or concentrations thereof) in a serial manner without additional user input steps to select the parameters of the analysis. Additionally, or alternatively, if the operator would like to analyze a different type of sample (e.g., a different medication), the operator can select a new medication button 1272 on the user interface 1260, where after the operator may select the type of medication, the overfill amount, and the concentration for the new sample.

An illustrative application for the systems described herein (e.g., the system 1200) is in the field of medicine, where the operator may be a pharmacy technician who is filling a prescription for a patient. The prescription indicates that a 60 ml syringe of hydromorphone mixed in saline is to be filled for a patient. The pharmacy technician can fill the syringe with the prescribed mixture, place the syringe in the enclosure 1210, select the sample type as "hydromorphone," (and possibly select an overfill and concentration, if applicable), and then select the verify button 1268 to verify that the sample in the syringe is indeed hydromorphone and/or that the concentration of the sample is a concentration specified by the operator. Many possible end uses for such a system are contemplated. For example, the system 1200 can be used to catch theft of medication, such as by testing samples of medication at any stage of their lifetime as the medication moves throughout a hospital or pharmacy setting. This, in turn, may help ensure that patients are getting a correct medication and a correct dosage of medication.

Other applications, including those in other industries, are also contemplated. For example, a verification approach similar to that described with reference to FIG. 12 can be used in the food industry, where a restaurant, for example, wants to determine if a food product is of a particular type and/or concentration for quality purposes to ensure that their inventory is correct. As another example, the sample verification approach described herein can be used to confirm control conditions in diagnostic assays. The identity and/or concentration of counterfeit goods can also be verified using the sample verification approach described herein. Examples of counterfeited goods include, without limitation, oils (e.g., food, petroleum, etc.), rubber (e.g., for tires), antiquities, arms and weaponry, and the like. In fact, optical spectroscopy can be used to verify the type and/or concentration of many different types of samples pertaining to various goods, such as, without limitation, ball bearings, beverages, biological samples, blood, cannabis products, ceramics, clothing, crops, curing agents, environmental pollutants, explosives, feed products, food, herbicides, jewelries, liquids, liquors, living matter, lotions, luxury goods, medicines, metals, nutritional supplements, oils, perfumes, personal care products, pesticides, petroleum, petroleum-derived liquids, pharmaceuticals, plastics, polyisocyanates, precious metal objects, reagents, rubbers, textiles, thermoplastic elastomers, thermoset polymers, etc.

It is to be appreciated that the systems described herein (e.g., the system 1200) may be used in other ways, such as diagnostics, where the results section 1270 may present additional and/or different results in response to optical spectroscopy of a sample within the enclosure 1210. For instance, the operator may not be required to select a sample type (e.g., a medication) beforehand, and, instead, may simply initiate an analysis (e.g., optical spectroscopy) of an unknown sample. In this example, the results section 1270 may specify what type of sample was detected using optical spectroscopy, and the concentration of that sample. This configuration may utilize a database of Raman spectra to compare the analysis results against to identify a type of sample and a concentration of the sample. In some cases, the results section 1270 may present a Raman spectra obtained from performing Raman spectroscopy on the sample, the Raman spectra being a "fingerprint" or "signature" of a particular material or sample type.

In view of the example system(s) described above, example process(es) that can be implemented in accordance with the disclosed subject matter can be better appreciated with reference to flowcharts in FIG. 13-FIG. 17. For purposes of simplicity of explanation, example processes disclosed herein are presented and described as a series of acts; however, it is to be understood and appreciated that the claimed subject matter is not limited by the order of acts, as some acts may occur in different orders and/or concurrently with other acts from that shown and described herein. For example, one or more example processes disclosed herein could alternatively be represented as a series of interrelated states or events, such as in a state diagram. Moreover, interaction diagram(s) may represent processes in accordance with the disclosed subject matter when disparate entities enact disparate portions of the processes. Furthermore, not all illustrated acts may be required to implement a described example process in accordance with the subject specification. Further yet, two or more of the disclosed example processes can be implemented in combination with each other, to accomplish one or more aspects herein described. It should be further appreciated that the example processes disclosed throughout the subject specification are capable of being stored on an article of manufacture (e.g., a computer-readable medium) to allow transporting and transferring such processes to computers for execution, and thus implementation, by a processor or for storage in a memory.

Figure 13:
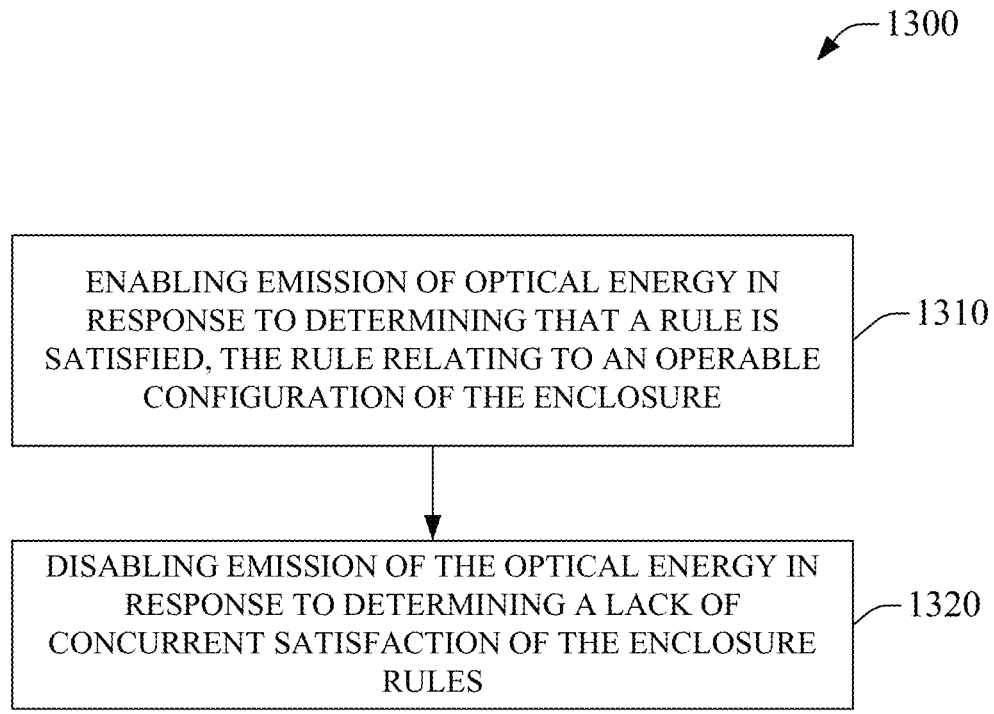
FIG. 13 depicts an example process facilitating release of optical interrogation energy based on satisfaction of a rule for an enclosed benchtop analytical device in accordance with aspects of the subject disclosure.

FIG. 13 illustrates a process 1300 facilitating release of optical interrogation energy based on satisfaction of a rule for an enclosed benchtop analytical device in accordance with aspects of the subject disclosure. At 1310, process 1300 can include enabling emission of optical energy. The enabling can be in response to determining that a rule is satisfied, the rule relating to an operable configuration of the enclosure.

In an aspect, a Raman spectrometer can interrogate a sample by emitting optical energy, into or onto a sample. Optical energy can be returned from the sample that is characteristic of the molecular composition of the sample. A rule related to an operable configuration of the enclosure can be determined to be satisfied when the lid is in a closed position relative to the body of the enclosure. In an aspect, this can allow designation of procedures, tolerances, and safety measures to be automatically monitored before allowing the analysis to proceed. As an example, a contact sensor can verify that an enclosure is closed before allowing a release of laser light to interrogate a sample, which can prevent the laser emission while the enclosure is not closed to protect an operator.

At 1320, process 1300 can include disabling emission of the optical energy in response to determining a lack of satisfaction of the rule. In an aspect, the optical energy can be stopped or shunted in response to determining that a rule is no longer satisfied. A compliance component, e.g., 612, 712, 812, 912, etc., can receive input from various sensors, monitors, user inputs, etc., to coordinate a release of a hold on optical energy to begin an analysis or halt an ongoing analysis.

Figure 14:
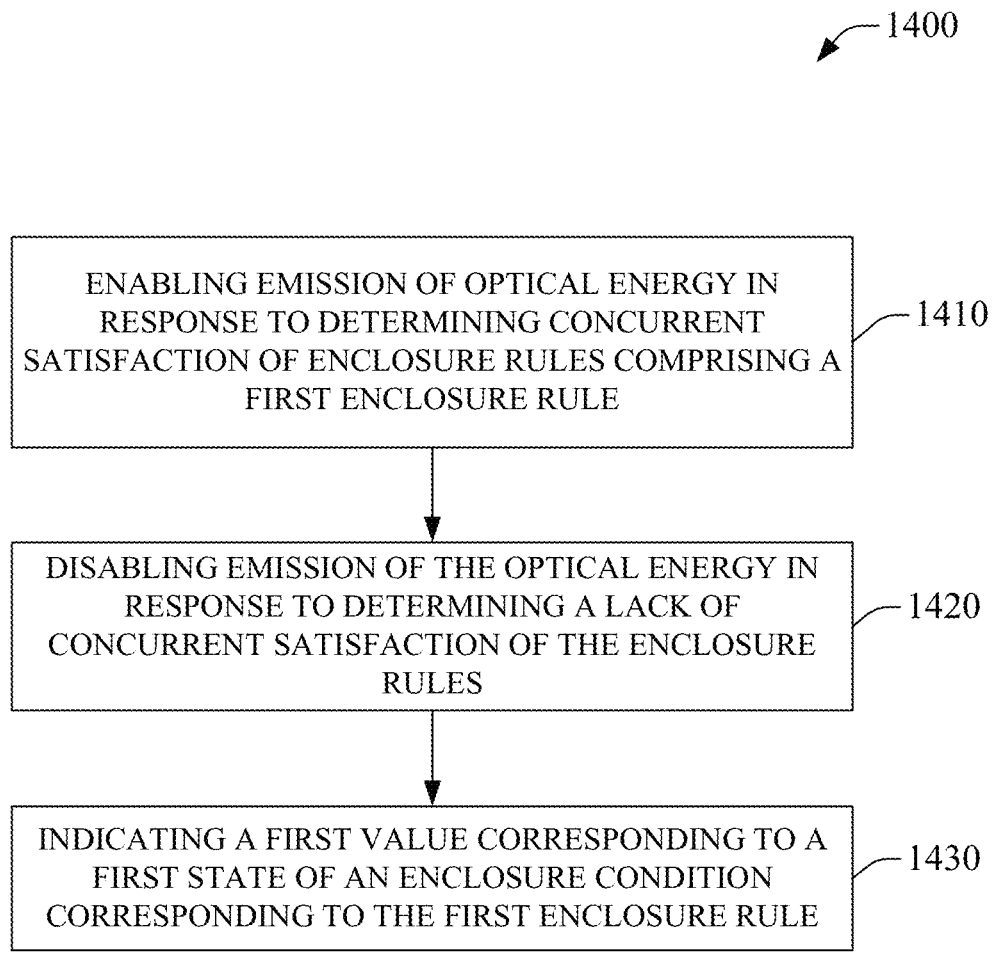
FIG. 14 depicts an example process facilitating release of optical interrogation energy based on satisfaction of rules for an enclosed benchtop analytical device in accordance with aspects of the subject disclosure.

As an example, an operator can place a sample in an enclosure having a contact sensor to detect closure of the lid of the enclosure. The example operator can then place a sample (e.g., a packaged sample) on or in the sample presentation component (e.g., on a sample plate), and the operator can close the lid of the enclosure to start the analysis. In this example, the compliance component can determine that the enclosure is properly closed before the analysis is allowed to proceed. Further, when a rule transitions from "in compliance" to "out of compliance" (e.g., the enclosure is opened), the interrogation beam can be shut off at block 1320. This can serve to protect the operator of the benchtop analytical device, protect the optical sensor of the instrument, ensure data quality, etc. FIG. 14 illustrates a process 1400 facilitating release of optical interrogation energy based on satisfaction of rules for an enclosed benchtop analytical device in accordance with aspects of the subject disclosure. At 1410, process 1400 can include enabling emission of optical energy. The enabling can be in response to determining concurrent satisfaction of rules including a first rule. The first rule can be related to determining contact between an optical element of a Raman spectroscopy probe and a sample. The first rule can be related to determining that the enclosure is closed.

In an aspect, a Raman spectrometer can interrogate a sample by emitting optical energy, into or onto a sample. Optical energy can be returned from the sample that is characteristic of the molecular composition of the sample. A first rule related to the contact can be determined to be satisfied when a probe, e.g., probe 102, 302, 402, 502, 602, 702, 802, 902, 1002, 1102, 1202, etc., is in contact with a sample, e.g., is pressed against a solid sample, inserted into a liquid or gas sample, etc. Where this first rule is part of a group of rules, and the group of rules is determined to be concurrently satisfied, the release of optical energy for interrogation of a sample can be enabled. A first rule related to a closed state of the enclosure can be determined to be satisfied when the lid is in a closed position relative to the body of the enclosure. In an aspect, this can allow designation of procedures, tolerances, and safety measures to be automatically monitored before allowing the analysis to proceed. As an example, a contact sensor can verify that an enclosure is closed before allowing a release of laser light to interrogate a sample, which can prevent the laser emission while the enclosure is not closed to protect an operator. Additional rules of the group of rules can be determined to be concurrently satisfied at 1410. For example, a rule relating to an operator being logged into a user account can be monitored to determine if the rule is satisfied concurrently with the first rule. As another example, a contact sensor can verify that an enclosure is closed before allowing via the probe to interrogate a sample. As another example, a light sensor can be monitored to ensure the sample is in darkness before the analysis can proceed, which can reduce artifacts in the spectral results that can occur when ambient light is present. As a further example, a temperature within the enclosure can be monitored (e.g., using a temperature sensor) to allow a sample to be at a known state before the analysis is enabled to proceed, which can reduce variation between analytical runs that can result from operators opening and closing an enclosure between runs. A compliance component can receive input from various sensors, monitors, user inputs, etc., to coordinate a release of a hold on an analysis, e.g., the analysis can occur in response to the concurrent satisfaction of one or more compliance rules. As another example, an operator can place a sample in an enclosure having an imaging system and a sample contact sensor. The example operator can then position a Raman probe at an area of interest on the sample. The imaging system can then be switched to a non-illumination mode to reduce light pollution and the example Raman probe can be advanced against the sample. In this example, the compliance component can determine that the enclosure is properly closed, that concurrently the illumination source is off, and can wait for the contact sensor to concurrently indicate that the Raman probe has contacted the sample. Upon the sample being contacted by the Raman probe, the contact sensor can indicate that contact has been made, which can satisfy a contact rule concurrently with the lights being off and the enclosure being closed, and can result in the analysis being allowed to proceed, e.g., the concurrent satisfaction of the conditions can start the analysis. This can allow an operator to simply place the sample, close the door, position the sample via a camera, and move the probe to contact the sample, whereupon the analysis is triggered and the operator can begin the subsequent analysis. Moreover, expanding the prior example, an array of samples, e.g., placed on a 96-well plate, etc., can be placed in embodiments of the disclosed subject matter, the enclosure can be closed, the operator can move, with the help of an internal video camera and illuminator, the probe to the first of the 96 wells in the plate and press a start button. In response, the example system can shut off the illuminator and begin a stage translation process to bring the probe into contact with each well of the 96-well plate sequentially. The example compliance component can verify that the enclosure is closed, that the illuminator is off, and can enable the Raman interrogation laser only when the probe is determined to be in contact with the sample plate, e.g., at each well as the translation process cycles the probe contact with each well, concurrent with the illuminator being off and the enclosure being closed.

At 1420, process 1400 can include disabling emission of the optical energy in response to determining a lack of concurrent satisfaction of the rules. In an aspect, the optical energy can be stopped or shunted in response to determining that a rule of the rules is no longer satisfied. Between 1410 and 1420, this can result in releasing optical energy only when the rules are simultaneously satisfied. A compliance component, e.g., 612, 712, 812, 912, etc., can receive input from various sensors, monitors, user inputs, etc., to coordinate a release of a hold on optical energy to begin an analysis, e.g., the analysis can occur in response to the concurrent satisfaction of one or more compliance rules.

As an example, an operator can place a sample in an enclosure having an imaging system and a sample contact sensor. The example operator can then position a Raman probe at an area of interest on the sample. The imaging system can then be switched to a non-illumination mode to reduce light pollution and the example Raman probe can be advanced against the sample. In this example, the compliance component can determine that the enclosure is properly closed, that concurrently the illumination source is off, and can wait for the contact sensor to indicate concurrently that the Raman probe has contacted the sample. Upon the sample being contacted by the Raman probe, the contact sensor can indicate that contact has been made, which can satisfy a contact rule concurrently with the lights being off, and the enclosure being closed, and can result in the analysis being allowed to proceed, e.g., the concurrent satisfaction of the conditions can start the analysis. This can allow an operator to simply place the sample, close the door, position the sample via a camera, and move the probe to contact the sample, whereupon the analysis is triggered and the operator can begin the subsequent analysis. Further, when the probe is retracted from the sample, the enclosure is opened, or the illumination source is reactivated, the interrogation beam can be shut off. This can serve to protect the operator of the instrument, protect the optical sensor of the instrument, ensure data quality, etc. Moreover, an array of samples, e.g., placed on a 96-well plate, etc., can be placed in embodiments of the disclosed subject matter, the enclosure can be closed, the operator can move, with the help of an internal video camera and illuminator, the probe to the first of the 96 wells in the plate and press a start button. In response, the example system can shut off the illuminator and begin a stage translation process to bring the probe into contact with each well of the 96-well plate sequentially. The example compliance component can verify that the enclosure is closed, that the illuminator is off, and can enable the Raman interrogation laser only when the probe is determined to be in contact with the sample plate, e.g., at each well as the translation process cycles the probe contact with each well, concurrent with the illuminator being off and the enclosure being closed. As such, should the enclosure be opened, the compliance component can prevent the release of laser energy.

At 1430, process 1400 can include indicating a first value corresponding to a first state of an enclosure condition corresponding to the first rule. At this point process 1400 can end. This can allow access to the first value by other systems/components, operators, etc. As an example, where the first rule relates to determining contact between the optical element of a Raman probe and the sample, the first value can be a distance between the probe and the sample, between the probe and the sample stage, a proximity metric of the probe to the sample, a depth of insertion of the probe into a flow cell, an amount of pressure measured between the probe and the sample stage, etc. The first value can guide additional actions, e.g., where the pressure between the probe and the sample plate transitions a threshold value, the distance between the probe and sample plate can be increased to prevent damage to the optical element of the probe, etc.

In some embodiments, acquisition of optical spectrums can be facilitated by process 1400. In some embodiments, a wireless link between a mobile device or other user equipment and the enclosed benchtop Raman spectrometer can enable control of aspects of the enclosed benchtop Raman spectrometer, for example, allowing modification, creation, deletion, etc., of rules and/or groups of rules. In another embodiment, a wired link between a user equipment and the enclosed benchtop Raman spectrometer can similarly enable control of aspects of the enclosed benchtop Raman spectrometer.

Figure 15:
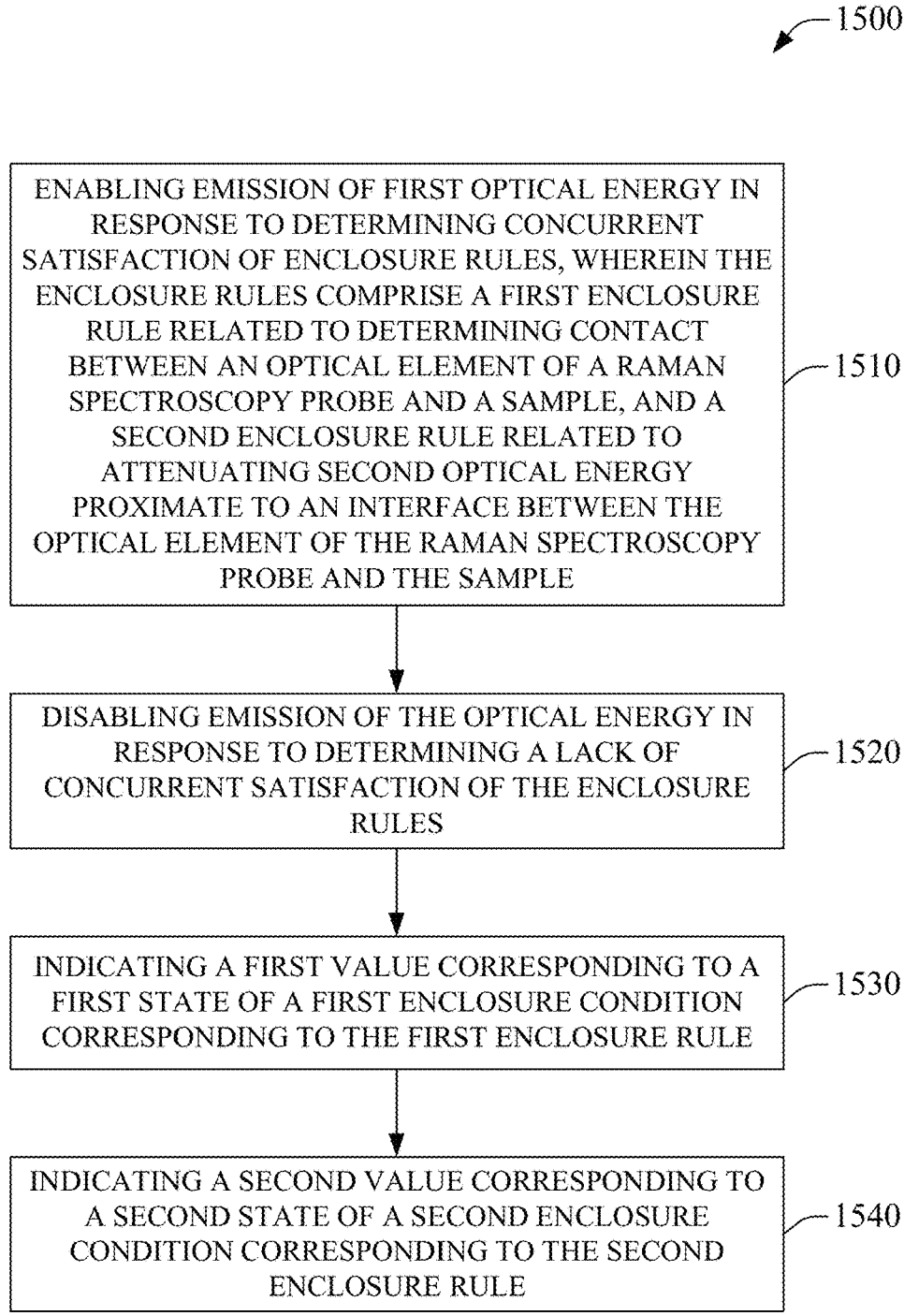
FIG. 15 illustrates an example process enabling emission of first interrogating optical energy based on an indication of contact between a probe and a sample and a concurrent indication of sufficiently attenuated non-interrogation optical energy in accordance with aspects of the subject disclosure.

FIG. 15 illustrates a process 1500 enabling emission of first interrogating optical energy based on an indication of contact between a probe and a sample and a concurrent indication of sufficiently attenuated non-interrogation optical energy in accordance with aspects of the subject disclosure. At 1510, process 1500 can include enabling emission of optical energy. The enabling can be in response to determining concurrent satisfaction of rules including a first rule and a second rule. The first rule can be related to determining contact between an optical element of a Raman spectroscopy probe and a sample. The second rule can be related to second optical energy proximate to the interface between the optical element and the sample.

A first rule related to the contact can be determined to be satisfied when a probe, e.g., probe 102, 302, 420, 502, 602, 702, 802, 902, 1002, 1102, 1202, etc., is in contact with a sample, e.g., is pressed against a solid sample, inserted into a liquid or gas sample, etc. The first rule can be satisfied when the probe is in contact with the sample to be tested. A second rule can relate to attenuation of ambient light in the interior of the enclosure. In an aspect, for example where the interior of the enclosure is monitored by an imaging device using an illuminator, e.g., 730/740, 830/840, 930/940, etc., it can be desirable to have the illuminator not emitting light that can be detected at the detector of the Raman spectrometer during interrogation of a sample. As such, the second rule can validate that the illuminator is off, that ambient light is below a threshold level, etc., within the enclosure, and more particularly at the sample-probe interface where stray light could affect spectroscopy results. Where this first rule is part of a group of rules, the second rule is part of the group of rules, and the group of rules is determined to be concurrently satisfied, the release of optical energy for interrogation of a sample can be enabled.

At 1520, process 1500 can include disabling emission of the optical energy in response to determining a lack of concurrent satisfaction of the rules. In an aspect, the optical energy can be stopped or shunted in response to determining that a rule, e.g., the first rule, the second rule, etc., of the rules is not being concurrently satisfied. This can result in releasing optical energy if, and only if, the group of rules are simultaneously satisfied. A compliance component, e.g., 612, 712, 812, 912, etc., can receive input from various sensors, monitors, user inputs, etc., to coordinate a release of a hold on optical energy to begin an analysis, e.g., the analysis can occur in response to the concurrent satisfaction of one or more compliance rules.

At 1530, process 1500 can include indicating a first value corresponding to a first state of a first enclosure condition corresponding to the first rule. This can allow access to the first value by other systems/components, operators, etc. As an example, where the first rule relates to determining contact between the optical element of a Raman probe and the sample, the first value can be a distance between the probe and the sample, between the probe and the sample stage, a proximity metric of the probe to the sample, a depth of insertion of the probe into a flow cell, an amount of pressure measured between the probe and the sample stage, etc. The first value can guide additional actions, e.g., where the pressure between the probe and the sample plate transitions a threshold value, the distance between the probe and sample plate can be increased to prevent damage to the optical element of the probe, etc.

At 1540, process 1500 can include indicating a second value corresponding to a second state of a second enclosure condition corresponding to the second rule. At this point process 1500 can end. This can allow access to the second value by other systems/components, operators, etc. As an example, where the second rule relates to determining ambient optical energy within the enclosure, the second value can be a measure of optical energy at a time, a time value indicating a rate of optical energy attenuation, etc. The second value can guide additional actions, e.g., where UV light causes a sample to fluoresce to facilitate placement of the probe relative to the sample, the fluorescence can decrease at a measurable rate, which measurable rate can be reflected in the second value. As such, this example second value can be employed, for example, by a timing delay component, e.g., included in the compliance component, etc., to delay onset of an optical analysis to allow for the fluorescence to drop below a threshold level to improve the results of the acquired spectral information.

Figure 16:
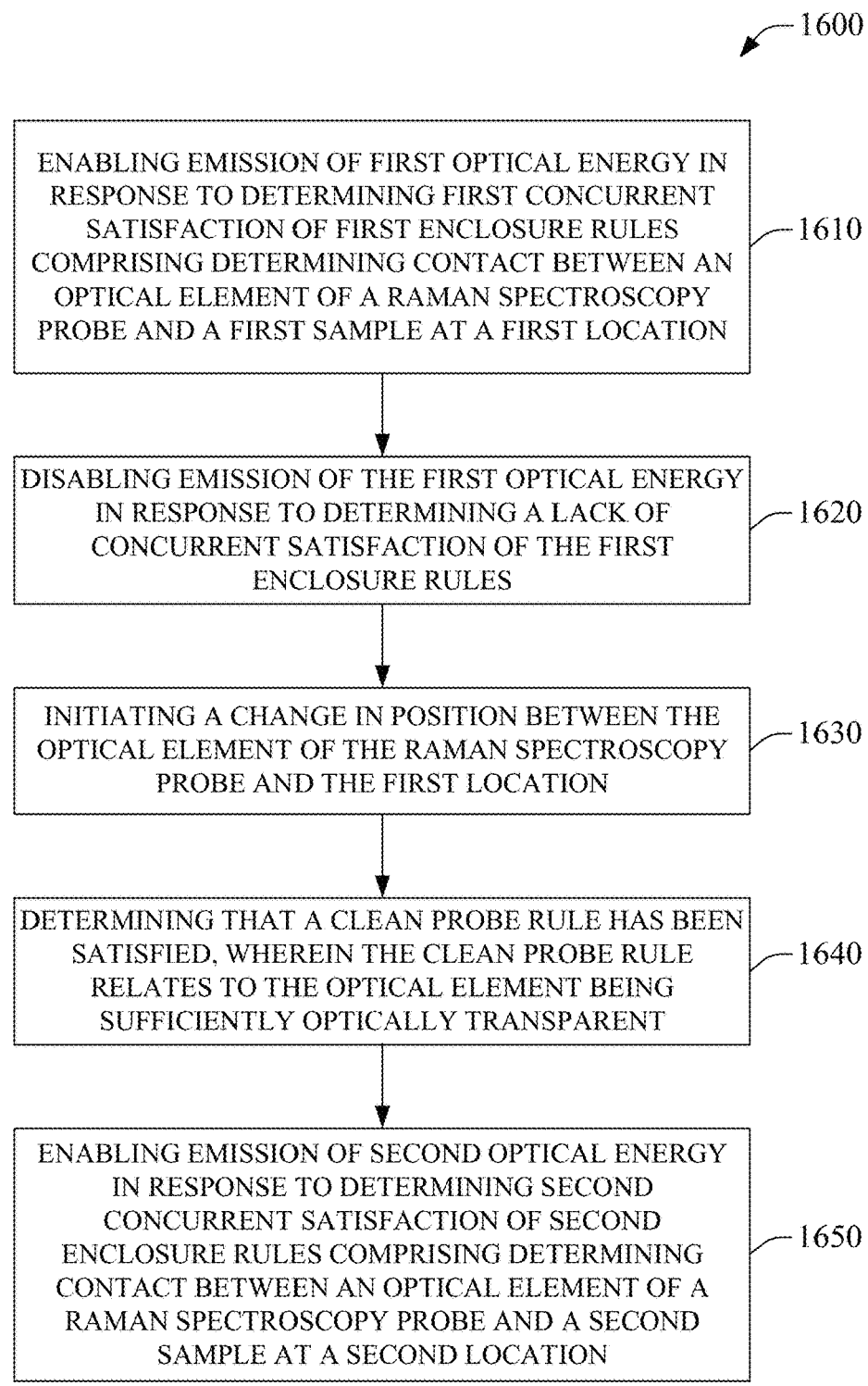
FIG. 16 illustrates an example process facilitating sequential optical interrogation of samples at different sample locations within an enclosed benchtop analytical device in accordance with aspects of the subject disclosure.

FIG. 16 illustrates a process 1600 that facilitating sequential optical interrogation of samples at different sample locations within an enclosed benchtop analytical device in accordance with aspects of the subject disclosure. At 1610, process 1600 can include enabling emission of first optical energy. The enabling can be in response to determining concurrent satisfaction of first rules including determining contact between an optical element of a Raman spectroscopy probe and a sample at a first location. Contact can be determined to be satisfied when a probe, e.g., probe 102, 302, 420, 502, 602, 702, 802, 902, 1002, 1102, 1202, etc., is in contact with a sample, e.g., is pressed against a solid sample, inserted into a liquid or gas sample, etc.

At 1620, process 1600 can include disabling emission of the optical energy in response to determining a lack of concurrent satisfaction of the first rules. In an aspect, the optical energy can be stopped or shunted in response to determining that the first rules are not being concurrently satisfied. This can result in releasing optical energy if, and only if, the first rules are simultaneously satisfied. A compliance component, e.g., 612, 712, 812, 912, etc., can receive input from various sensors, monitors, user inputs, etc., to coordinate a release of a hold on optical energy to begin an analysis, e.g., the analysis can occur in response to the concurrent satisfaction of one or more compliance rules of the first rules.

At 1630, process 1600 can include indicating a change in position between the optical element of the Raman spectroscopy probe and the first location. In an aspect, the change in position can occur subsequent to the probe not being in contact with a solid sample to prevent damage to the probe, although it will be noted that where the probe is in a gas or liquid, the change in position can occur without removing the probe form contact with the sample where the gas or liquid is unlikely to damage the probe. In some embodiments, the change in position can correlate to distances between wells included in a multi-well plate, e.g., a 384-, 96-, 48-, 24-, 12-, 6-well plate sample container, etc. This can enable analysis of samples in one or more wells of the multi-well plate.

At 1640, process 1600 can include determining that a clean probe rule has been satisfied. The clean probe rule can relate to cleaning of the optical element of the Raman spectroscopy probe between contacts with a sample(s), e.g., the optical element can be determined to be optically transparent in Raman relevant regions to satisfy the clean probe rule. In some embodiments, where cleaning of the probe fails, the probe can be exchanged for a new or otherwise clean probe. This new or other clean probe can satisfy the clean probe rule.

At 1650, process 1600 can include enabling emission of second optical energy. The enabling can be in response to determining concurrent satisfaction of second rules including determining contact between an optical element of a Raman spectroscopy probe and a sample at a second location. At this point process 1600 can end. In an aspect, the second capture of a second Raman spectrum at a second location of a sample, or another sample, can occur automatically in response to the second rules being determined to be concurrently satisfied. In an example, where a probe is in contact with a sample in a first well of a plate, a first spectrum can be captured where the first rules are concurrently satisfied. Upon retracting the probe from the first well, the first rules can fail to be satisfied and the Raman laser can correspondingly be shunted. The plate can be moved and the probe can be cleaned. The probe can then be brought into contact with a sample in a second well of the plate in a manner that concurrently satisfies second rules, whereby shunting of the laser is ended and a second Raman spectrum can be captured.

Figure 17:
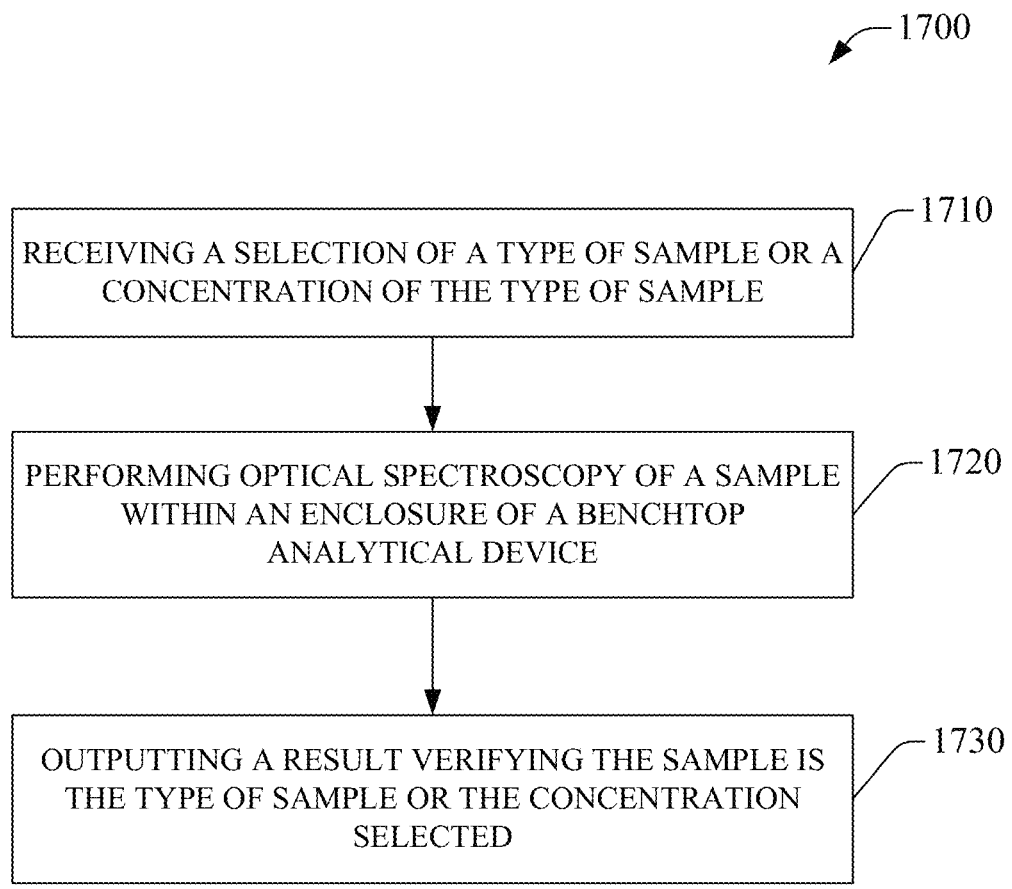
FIG. 17 illustrates an example process enabling verification of a type of sample and/or a concentration of the sample by performing optical spectroscopy of the sample within an enclosure of a benchtop analytical device in accordance with aspects of the subject disclosure.

FIG. 17 illustrates an example process 1700 enabling verification of a type of sample and/or a concentration of the sample by performing optical spectroscopy of the sample within an enclosure of a benchtop analytical device in accordance with aspects of the subject disclosure.

At 1710, a computer coupled to a benchtop analytical device may receive, via a user interface, a selection of (i) a type of sample among multiple available types of samples or (ii) a concentration of the type of sample. For example, the computer may maintain a database of available types of samples (e.g., types of medication) for selection, and an operator may select one of those types of samples in order to verify a sample in the operator's possession is the type of sample, and/or to verify that the sample in the operator's possession is of a particular concentration. FIG. 12 shows an example user interface 1260 for this purpose.

At 1720, optical spectroscopy of a sample within an enclosure of the benchtop analytical device may be performed by emitting optical energy from a probe within the enclosure toward the sample. For instance, the operator may place a sample within the enclosure of the benchtop analytical device, may close the lid of the enclosure, and commence optical spectroscopy of the sample by pressing a button (e.g., a verify button, start button, etc.).

At 1730, the computer may output, via the user interface, a result verifying (i) that the sample is the type of sample or (ii) the sample is of a concentration corresponding to (e.g., equal to, within a tolerance of, etc.) the selected concentration.

The process 1700 may be implemented in combination with any of the features and functionality described herein for operational use of the disclosed benchtop analytical device. In particular, the features and functionality described with reference to FIG. 12 can be included in the context of the process 1700.

Figure 18:
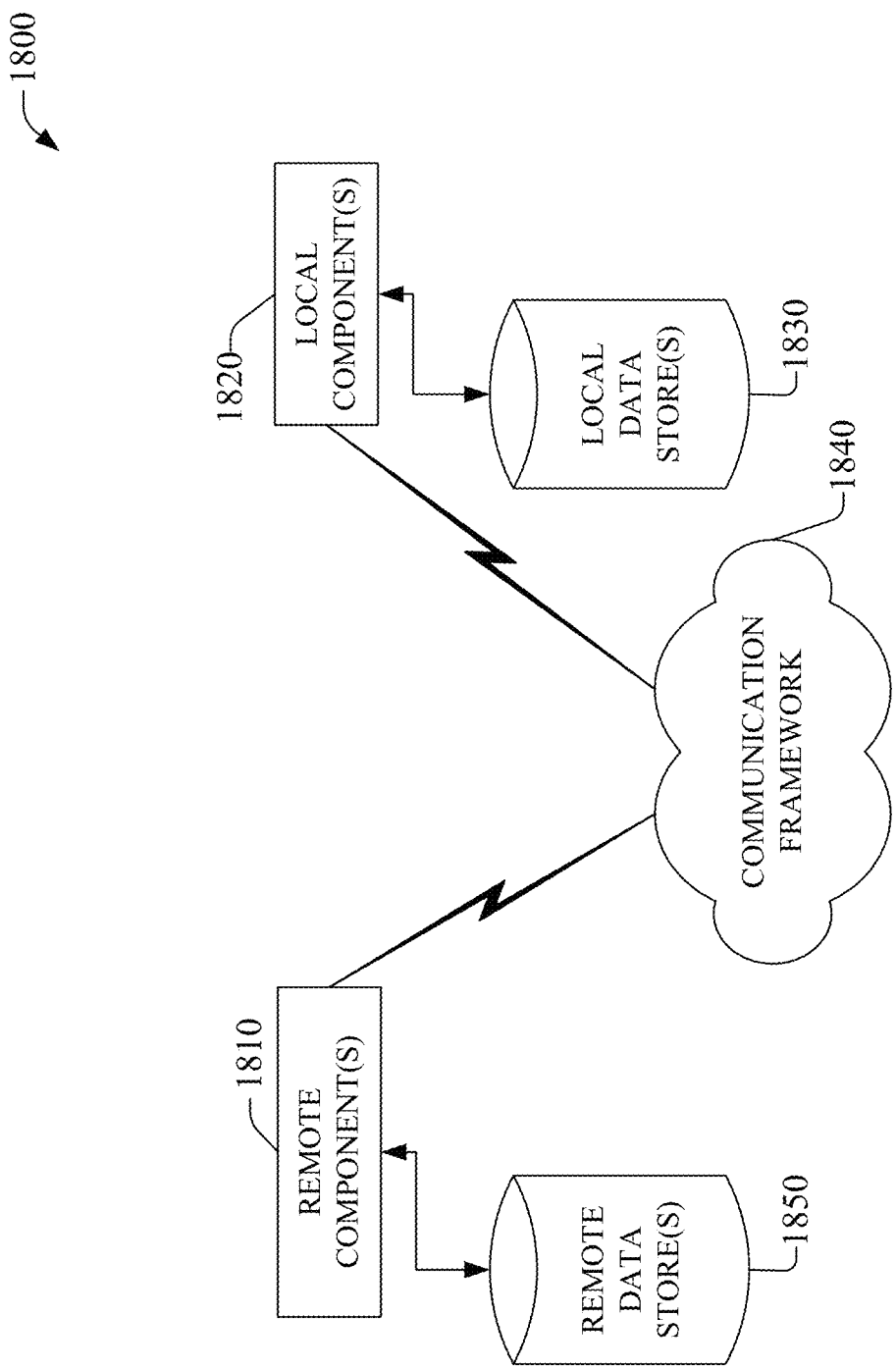
FIG. 18 depicts an example schematic block diagram of a computing environment with which the disclosed subject matter can interact.

FIG. 18 is a schematic block diagram of a computing environment 1800 with which the disclosed subject matter can interact. The system 1800 includes one or more remote component(s) 1810. The remote component(s) 1810 can be hardware and/or software (e.g., threads, processes, computing devices). In some embodiments, remote component(s) 1810 can include servers, personal servers, etc. As an example, remote component(s) 1810 can be a remote server, a controller component, a remotely located compliance component 612, 712, 812, 912, etc., user equipment, laboratory information management system (LIMS) component, etc.

The system 1800 also includes one or more local component(s) 1820. The local component(s) 1820 can be hardware and/or software (e.g., threads, processes, computing devices). In some embodiments, local component(s) 1820 can include, for example, a local compliance component 612, 712, 812, 912, etc., imaging component 130, 230, 330, 430, etc., sample presentation component 620, 720, 820, 920, 1020, 1120, 1220, etc., stage motion component 1022, 1122, etc.

One possible communication between a remote component(s) 1810 and a local component(s) 1820 can be in the form of a data packet adapted to be transmitted between two or more computer processes. Another possible communication between a remote component(s) 1810 and a local component(s) 1820 can be in the form of circuit-switched data adapted to be transmitted between two or more computer processes in radio time slots. The system 1800 includes a communication framework 1840 that can be employed to facilitate communications between the remote component(s) 1810 and the local component(s) 1820, and can include an air interface, e.g., Uu interface of a UMTS network. Remote component(s) 1810 can be operably connected to one or more remote data store(s) 1850, such as a hard drive, SIM card, device memory, etc., that can be employed to store information on the remote component(s) 1810 side of communication framework 1840. Similarly, local component(s) 1820 can be operably connected to one or more local data store(s) 1830, that can be employed to store information on the local component(s) 1820 side of communication framework 1840.

Figure 19:
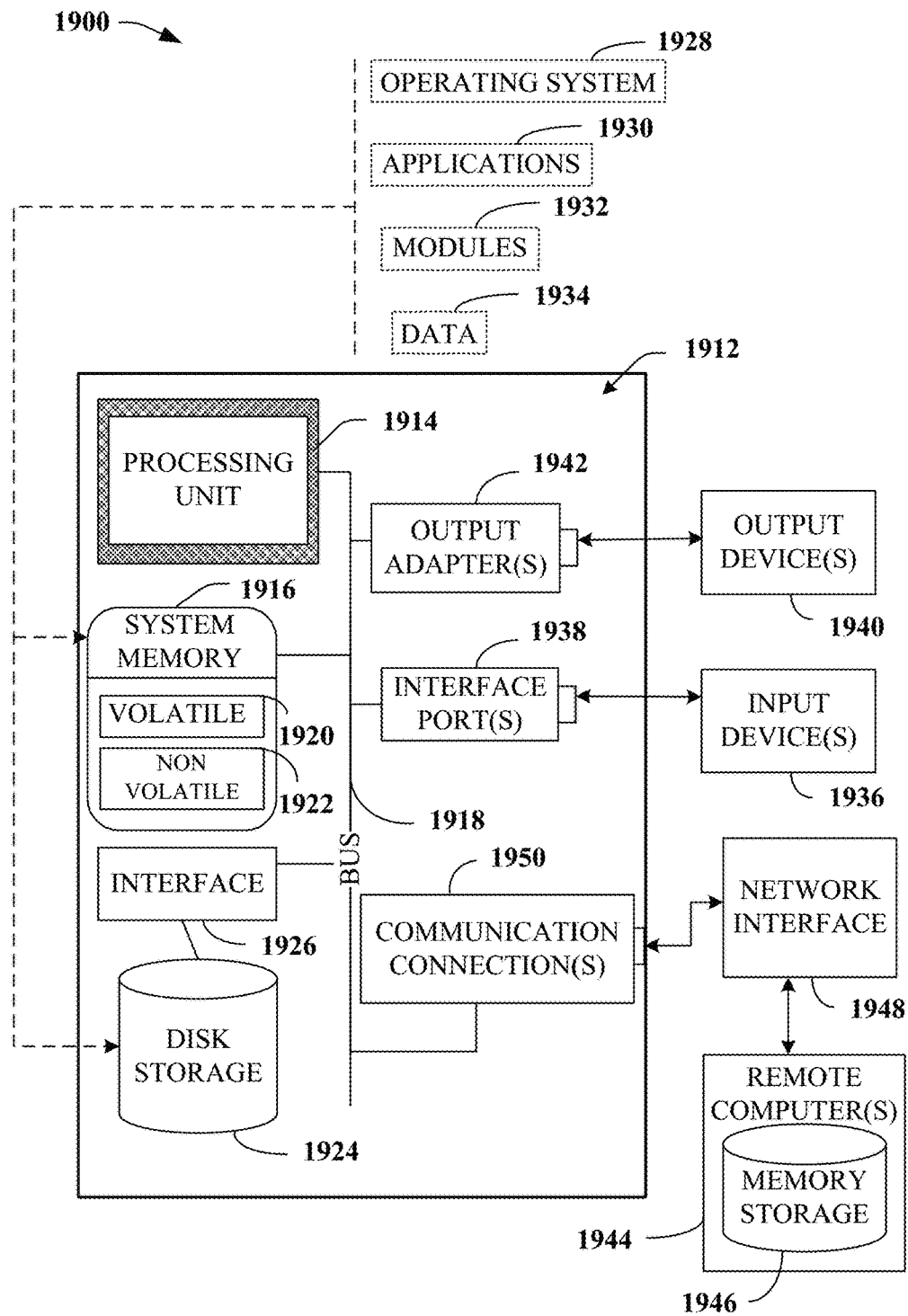
FIG. 19 illustrates an example block diagram of a computing system operable to execute the disclosed systems and processes in accordance with some embodiments.

In order to provide a context for the various aspects of the disclosed subject matter, FIG. 19, and the following discussion, are intended to provide a brief, general description of a suitable environment in which the various aspects of the disclosed subject matter can be implemented. While the subject matter has been described above in the general context of computer-executable instructions of a computer program that runs on a computer and/or computers, those skilled in the art will recognize that the disclosed subject matter also can be implemented in combination with other program modules. Generally, program modules include routines, programs, components, data structures, etc. that performs particular tasks and/or implement particular abstract data types.

In the subject specification, terms such as "store," "storage," "data store," data storage," "database," and substantially any other information storage component relevant to operation and functionality of a component, refer to "memory components," or entities embodied in a "memory" or components including the memory. It is noted that the memory components described herein can be either volatile memory or nonvolatile memory, or can include both volatile and nonvolatile memory, by way of illustration, and not limitation, volatile memory 1920 (see below), non-volatile memory 1922 (see below), disk storage 1924 (see below), and memory storage 1946 (see below). Further, nonvolatile memory can be included in read only memory, programmable read only memory, electrically programmable read only memory, electrically erasable read only memory, or flash memory. Volatile memory can include random access memory, which acts as external cache memory. By way of illustration and not limitation, random access memory is available in many forms such as synchronous random access memory , dynamic random access memory, synchronous dynamic random access memory, double data rate synchronous dynamic random access memory, enhanced synchronous dynamic random access memory, Synchlink dynamic random access memory, and direct Rambus random access memory. Additionally, the disclosed memory components of systems or processes herein are intended to include, without being limited to including, these and any other suitable types of memory.

Moreover, it is noted that the disclosed subject matter can be practiced with other computer system configurations, including single-processor or multiprocessor computer systems, mini-computing devices, mainframe computers, as well as personal computers, hand-held computing devices (e.g., personal digital assistant, phone, watch, tablet computers, netbook computers, . . . ), microprocessor-based or programmable consumer or industrial electronics, and the like. The illustrated aspects can also be practiced in distributed computing environments where tasks are performed by remote processing devices that are linked through a communications network; however, some if not all aspects of the subject disclosure can be practiced on stand-alone computers. In a distributed computing environment, program modules can be located in both local and remote memory storage devices.

FIG. 19 illustrates a block diagram of a computing system 1900 operable to execute the disclosed systems and processes in accordance with some embodiments. Computer 1912, which can be, for example, included in compliance component 612-912, etc., sample presentation component 620-1220, etc., stage motion component 1022-1122, etc., state interaction component 1024-1124, etc., enclosure 110, 310, 410, 610-910, and 1210, etc., imaging component 630-930, etc., environmental control component 960, etc., includes a processing unit 1914, a system memory 1916, and a system bus 1918. System bus 1918 couples system components including, but not limited to, system memory 1916 to processing unit 1914. Processing unit 1914 can be any of various available processors. Dual microprocessors and other multiprocessor architectures also can be employed as processing unit 1914.

System bus 1918 can be any of several types of bus structure(s) including a memory bus or a memory controller, a peripheral bus or an external bus, and/or a local bus using any variety of available bus architectures including, but not limited to, industrial standard architecture, micro-channel architecture, extended industrial standard architecture, intelligent drive electronics, video electronics standards association local bus, peripheral component interconnect, card bus, universal serial bus, advanced graphics port, personal computer memory card international association bus, Firewire (Institute of Electrical and Electronics Engineers 1194), and small computer systems interface.

System memory 1916 can include volatile memory 1920 and nonvolatile memory 1922. A basic input/output system, containing routines to transfer information between elements within computer 1912, such as during start-up, can be stored in nonvolatile memory 1922. By way of illustration, and not limitation, nonvolatile memory 1922 can include read only memory, programmable read only memory, electrically programmable read only memory, electrically erasable read only memory, or flash memory. Volatile memory 1920 includes read only memory, which acts as external cache memory. By way of illustration and not limitation, read only memory is available in many forms such as synchronous random access memory, dynamic read only memory, synchronous dynamic read only memory, double data rate synchronous dynamic read only memory, enhanced synchronous dynamic read only memory, Synchlink dynamic read only memory, Rambus direct read only memory, direct Rambus dynamic read only memory, and Rambus dynamic read only memory.

Computer 1912 can also include removable/non-removable, volatile/non-volatile computer storage media. FIG. 19 illustrates, for example, disk storage 1824. Disk storage 1924 includes, but is not limited to, devices like a magnetic disk drive, floppy disk drive, tape drive, flash memory card, or memory stick. In addition, disk storage 1924 can include storage media separately or in combination with other storage media including, but not limited to, an optical disk drive such as a compact disk read only memory device, compact disk recordable drive, compact disk rewritable drive or a digital versatile disk read only memory. To facilitate connection of the disk storage devices 1924 to system bus 1918, a removable or non-removable interface is typically used, such as interface 1926.

Computing devices typically include a variety of media, which can include computer-readable storage media or communications media, which two terms are used herein differently from one another as follows.

Computer-readable storage media can be any available storage media that can be accessed by the computer and includes both volatile and nonvolatile media, removable and non-removable media. By way of example, and not limitation, computer-readable storage media can be implemented in connection with any process or technology for storage of information such as computer-readable instructions, program modules, structured data, or unstructured data. Computer-readable storage media can include, but are not limited to, read only memory, programmable read only memory, electrically programmable read only memory, electrically erasable read only memory, flash memory or other memory technology, compact disk read only memory, digital versatile disk or other optical disk storage, magnetic cassettes, magnetic tape, magnetic disk storage or other magnetic storage devices, or other tangible media which can be used to store desired information. In this regard, the term "tangible" herein as may be applied to storage, memory or computer-readable media, is to be understood to exclude only propagating intangible signals per se as a modifier and does not relinquish coverage of all standard storage, memory or computer-readable media that are not only propagating intangible signals per se. In an aspect, tangible media can include non-transitory media wherein the term "non-transitory" herein as may be applied to storage, memory or computer-readable media, is to be understood to exclude only propagating transitory signals per se as a modifier and does not relinquish coverage of all standard storage, memory or computer-readable media that are not only propagating transitory signals per se. Computer-readable storage media can be accessed by one or more local or remote computing devices, e.g., via access requests, queries or other data retrieval protocols, for a variety of operations with respect to the information stored by the medium. As such, for example, a computer-readable medium can include executable instructions stored thereon that, in response to execution, cause a system including a processor to perform operations, including: enabling emission of optical energy in response to determining concurrent satisfaction of a group of rules, e.g., via compliance component 612-912, etc.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

It can be noted that FIG. 19 describes software that acts as an intermediary between users and computer resources described in suitable operating environment 1900. Such software can include an operating system 1928. Operating system 1928, which can be stored on disk storage 1924, acts to control and allocate resources of computer system 1912. System applications 1930 take advantage of the management of resources by operating system 1928 through program modules 1932 and program data 1934 stored either in system memory 1916 or on disk storage 1924. It is to be noted that the disclosed subject matter can be implemented with various operating systems or combinations of operating systems.

A user can enter commands or information into computer 1912 through input device(s) 1936. In some embodiments, a user interface can allow entry of user preference information, etc., and can be embodied in a touch sensitive display panel, a mouse input GUI, a command line controlled interface, etc., allowing a user to interact with computer 1912. Input devices 1936 include, but are not limited to, a pointing device such as a mouse, trackball, stylus, touch pad, keyboard, microphone, joystick, game pad, satellite dish, scanner, TV tuner card, digital camera, digital video camera, web camera, cell phone, smartphone, tablet computer, etc. These and other input devices connect to processing unit 1914 through system bus 1918 by way of interface port(s) 1938. Interface port(s) 1938 include, for example, a serial port, a parallel port, a game port, a universal serial bus, an infrared port, a Bluetooth port, an IP port, or a logical port associated with a wireless service, etc. Output device(s) 1940 use some of the same type of ports as input device(s) 1936.

Thus, for example, a universal serial bus port can be used to provide input to computer 1912 and to output information from computer 1912 to an output device 1940. Output adapter 1942 is provided to illustrate that there are some output devices 1940 like monitors, speakers, and printers, among other output devices 1940, which use special adapters. Output adapters 1942 include, by way of illustration and not limitation, video and sound cards that provide means of connection between output device 1940 and system bus 1918. It should be noted that other devices and/or systems of devices provide both input and output capabilities such as remote computer(s) 1944.

Computer 1912 can operate in a networked environment using logical connections to one or more remote computers, such as remote computer(s) 1944. Remote computer(s) 1944 can be a personal computer, a server, a router, a network PC, cloud storage, a cloud service, code executing in a cloud-computing environment, a workstation, a microprocessor based appliance, a peer device, or other common network node and the like, and typically includes many or all of the elements described relative to computer 1912.

For purposes of brevity, only a memory storage device 1946 is illustrated with remote computer(s) 1944. Remote computer(s) 1944 is logically connected to computer 1912 through a network interface 1948 and then physically connected by way of communication connection 1950. Network interface 1948 encompasses wire and/or wireless communication networks such as local area networks and wide area networks. Local area network technologies include fiber distributed data interface, copper distributed data interface, Ethernet, Token Ring, Radius, Diameter, and the like. Wide area network technologies include, but are not limited to, point-to-point links, circuit-switching networks like integrated services digital networks and variations thereon, packet switching networks, and digital subscriber lines. As noted below, wireless technologies may be used in addition to or in place of the foregoing.

Communication connection(s) 1950 refer(s) to hardware/software employed to connect network interface 1948 to bus 1918. While communication connection 1950 is shown for illustrative clarity inside computer 1912, it can also be external to computer 1912. The hardware/software for connection to network interface 1948 can include, for example, internal and external technologies such as modems, including regular telephone grade modems, cable modems and digital subscriber line modems, integrated services digital network adapters, and Ethernet cards.

The above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the disclosed subject matter has been described in connection with various embodiments and corresponding Figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

As it employed in the subject specification, the term "processor" can refer to substantially any computing processing unit or device including, but not limited to including, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit, a digital signal processor, a field programmable gate array, a programmable logic controller, a complex programmable logic device, a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

As used in this application, the terms "component," "system," "platform," "layer," "selector," "interface," and the like are intended to refer to a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, a program, and/or a computer. By way of illustration and not limitation, both an application running on a server and the server can be a component. One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can include a processor therein to execute software or firmware that confers at least in part the functionality of the electronic components.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of" The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Moreover, terms like "user equipment (UE)," "mobile station," "mobile," subscriber station," "subscriber equipment," "access terminal," "terminal," "handset," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point," "AP," "base station," "Node B," "evolved Node B," "eNodeB," "home Node B," "home access point," and the like, are utilized interchangeably in the subject application, and refer to a wireless network component or appliance that serves and receives data, control, voice, video, sound, gaming, or substantially any data-stream or signaling-stream to and from a set of subscriber stations or provider enabled devices. Data and signaling streams can include packetized or frame-based flows.

Furthermore, the terms "user," "subscriber," "customer," "consumer," "prosumer," "agent," and the like are employed interchangeably throughout the subject specification, unless context warrants particular distinction(s) among the terms. It should be appreciated that such terms can refer to human entities or automated components (e.g., supported through artificial intelligence, as through a capacity to make inferences based on complex mathematical formalisms), that can provide simulated vision, sound recognition and so forth.

Aspects, features, or advantages of the subject matter can be exploited in substantially any, or any, wired, broadcast, wireless telecommunication, radio technology or network, or combinations thereof. Non-limiting examples of such technologies or networks include broadcast technologies (e.g., sub-Hertz, extremely low frequency, very low frequency, low frequency, medium frequency, high frequency, very high frequency, ultra-high frequency, super-high frequency, terahertz broadcasts, etc.); Ethernet; X.25; power-line-type networking, e.g., Powerline audio video Ethernet, etc.; femtocell technology; Wi-Fi; worldwide interoperability for microwave access; enhanced general packet radio service; third generation partnership project, long term evolution; third generation partnership project universal mobile telecommunications system; third generation partnership project 2, ultra mobile broadband; high speed packet access; high speed downlink packet access; high speed uplink packet access; enhanced data rates for global system for mobile communication evolution radio access network; universal mobile telecommunications system terrestrial radio access network; or long term evolution advanced.

What has been described above includes examples of systems and processes illustrative of the disclosed subject matter. It is, of course, not possible to describe every combination of components or processes herein. One of ordinary skill in the art may recognize that many further combinations and permutations of the claimed subject matter are possible.

What is claimed is:

1. A benchtop analytical device, comprising:
   an enclosure having a lid and a body, the lid being movable, relative to the body, between an opened position and a closed position, wherein, when the lid is in the closed position, the enclosure encloses:
      a probe mounted on the body of the enclosure to facilitate performing optical spectroscopy of a sample; and
      a sample presentation component to receive the sample for the performing of the optical spectroscopy;
   a processor; and
   a memory storing executable instructions that, when executed by the processor, cause the benchtop analytical device to:
      receive an indication that the lid of the enclosure is in the closed position;
      determine that a rule is satisfied, wherein the rule relates to an operable configuration of the enclosure based on the indication that the lid of the enclosure is in the closed position; and
      in response to determining that the rule is satisfied, cause emission of optical energy to perform the optical spectroscopy of the sample via the probe.

2. The benchtop analytical device of claim 1, wherein the executable instructions, when executed by the processor, further cause the benchtop analytical device to determine that a group of rules comprising the rule and a second rule is concurrently satisfied, wherein the optical spectroscopy is performed in response to determining that the group of rules is concurrently satisfied.

3. The benchtop analytical device of claim 2, wherein the second rule of the group of rules is related to determining that an operator of the benchtop analytical device has logged into a user account.

4. The benchtop analytical device of claim 1, wherein the sample presentation component comprises a sample plate to receive and support the sample within the enclosure.

5. The benchtop analytical device of claim 4, wherein:
   a plate retaining area is defined in the body of the enclosure;
   the probe is mounted within the plate retaining area;
   the sample plate is removably disposed in the plate retaining area and has at least one of:
      a sloped surface that slopes from a highest point at a periphery of the sample plate to a lowest point at a location adjacent to the probe when the sample plate is disposed on in the plate retaining area; or
      a flat surface with a recessed area defined in the flat surface of the sample plate, a portion of the recessed area positioned at a location adjacent to the probe when the sample plate is disposed in the plate retaining area.

6. The benchtop analytical device of claim 5, wherein:
   an aperture is defined in the sample plate at (i) the lowest point of the sloped surface or (ii) the portion of the recessed area; and
   the probe is vertically oriented, pointing in an upward direction, and disposed within the aperture to interrogate the sample from underneath the sample when the sample plate is disposed in the plate retaining area and when the sample is supported on a topside of the sample plate over the aperture.

7. The benchtop analytical device of claim 6, wherein the sample plate has the sloped surface, and a tip of the probe extends above the lowest point of the sloped surface when the sample plate is disposed in the plate retaining area.

8. The benchtop analytical device of claim 5, wherein the sample plate has the flat surface and the sample is to be placed in the recessed area prior to closing the lid of the enclosure.

9. The benchtop analytical device of claim 5, wherein the sample plate is a first sample plate that is exchangeable with a second sample plate that is different from the first sample plate.

10. The benchtop analytical device of claim 5, wherein the plate retaining area has a sloped surface that slopes from a highest point at a periphery of the plate retaining area to a lowest point adjacent to the probe.

11. A benchtop analytical device, comprising:
an enclosure having a lid and a body, the lid being movable, relative to the body, between an opened position and a closed position, wherein, when the lid is in the closed position, the enclosure encloses:
a probe mounted on the body of the enclosure to channel optical energy as part of performing optical spectroscopy of a sample; and
a sample presentation component to receive the sample; and
a compliance component that (i) enables release of the optical energy via the probe in response to determining that the lid of the enclosure is in the closed position and (ii) disables the release of the optical energy via the probe in response to determining that the lid of the enclosure is not in the closed position.

12. The benchtop analytical device of claim 11, wherein the compliance component enables the release of the optical energy via the probe in response to determining that a group of rules is concurrently satisfied, wherein a first rule of the group of rules is satisfied when the lid of the enclosure is in the closed position.

13. The benchtop analytical device of claim 12, wherein a second rule of the group of rules is satisfied when an operator of the benchtop analytical device has logged into a user account.

14. The benchtop analytical device of claim 11, wherein the sample presentation component comprises a sample plate to receive and support the sample within the enclosure.

15. The benchtop analytical device of claim 11, wherein, when the lid of the enclosure is in the closed position, the enclosure further encloses an adjustment mechanism that is usable by an operator of the benchtop analytical device, while the lid of the enclosure is in the opened position, to adjust a position of the sample presentation component relative to the probe.

16. The benchtop analytical device of claim 11, wherein the enclosure comprises a viewport made of a window material that attenuates transmission of the optical energy while enabling direct visualization of an interior of the enclosure when the lid is in the closed position.

17. The benchtop analytical device of claim 11, wherein the performing of the optical spectroscopy of the sample includes performing Raman spectroscopy of the sample.

18. A method comprising:
enabling, by a compliance component of a benchtop analytical device, release of optical energy via a probe in response to determining that a rule is satisfied, wherein the rule is satisfied based on a lid of an enclosure being in a closed position, the enclosure, when the lid is in the closed position, enclosing a sample presentation component and the probe, the probe performing optical spectroscopy of a sample that is in or on the sample presentation component by directing the optical energy toward the sample; and
disabling, by the compliance component, the release of the optical energy in response to determining that the rule is not satisfied.

19. The method of claim 18, wherein the compliance component enables the release of the optical energy in response to determining that a group of rules is concurrently satisfied, the group of rules including the rule and a second rule, the second rule being satisfied based on an operator of the benchtop analytical device having logged into a user account.

20. The method of claim 18, wherein the release of the optical energy is a sub step of performing Raman spectroscopy of the sample.

21. A method comprising:
receiving, via a user interface, a selection of (i) a type of sample among multiple available types of samples or (ii) a concentration of the type of sample;
performing optical spectroscopy of a sample within an enclosure of a benchtop analytical device by emitting optical energy from a probe within the enclosure toward the sample; and
outputting, via the user interface, a result verifying (i) that the sample is the type of sample or (ii) the concentration of the sample.

22. The method of claim 21, further comprising:
determining, by a compliance component of the benchtop analytical device, that a rule is satisfied, wherein the rule is satisfied based on a lid of the enclosure being in a closed position; and
enabling, by the compliance component, release of the optical energy via the probe to perform the optical spectroscopy in response to the determining that the rule is satisfied.

* * * * *